United States Patent
Cooke et al.

(10) Patent No.: US 8,759,352 B2
(45) Date of Patent: Jun. 24, 2014

(54) 1-(4-UREIDOBENZOYL)PIPERAZINE DERIVATIVES

(75) Inventors: Andrew John Cooke, East Kilbride (GB); David Jonathan Bennett, Edinburgh (GB); Andrew Stanley Edwards, Campsie Glen (GB); Andrew Laird Roughton, Port Hope (CA); Irina Neagu, Belmont, MA (US); Jui-Hsiang Chan, West Windsor, NJ (US); Koc-Kan Ho, West Windsor, NJ (US); Nasrin Ansari, Monmouth Junction, NJ (US); Michelle Lee Morris, Lawrenceville, NJ (US); Yajing Rong, Yardley, PA (US); Michael Ohlmeyer, Plainsboro, NJ (US)

(73) Assignees: Merck Sharp & Dohme B.V., Oss (NL); Pharmacopeia LLC., San Diego, CA (US)

( * ) Notice: Subject to any disclaimer, the term of this patent is extended or adjusted under 35 U.S.C. 154(b) by 335 days.

(21) Appl. No.: 13/060,730

(22) PCT Filed: Aug. 26, 2009

(86) PCT No.: PCT/US2009/055035
§ 371 (c)(1),
(2), (4) Date: Sep. 7, 2011

(87) PCT Pub. No.: WO2010/025179
PCT Pub. Date: Mar. 4, 2010

(65) Prior Publication Data
US 2012/0015958 A1 Jan. 19, 2012

Related U.S. Application Data

(60) Provisional application No. 61/092,469, filed on Aug. 28, 2008.

(51) Int. Cl.
| | | |
|---|---|---|
| *A61K 31/496* | (2006.01) | |
| *C07D 213/56* | (2006.01) | |
| *C07D 263/34* | (2006.01) | |
| *C07D 277/56* | (2006.01) | |
| *C07D 307/68* | (2006.01) | |

(52) U.S. Cl.
USPC ........... 514/253.13; 514/254.02; 514/254.05; 514/254.1; 544/365; 544/369; 544/371; 544/379

(58) Field of Classification Search
None
See application file for complete search history.

(56) References Cited

U.S. PATENT DOCUMENTS 8,357,679 B2 * 1/2013 Cooke et al. .......... 514/218

FOREIGN PATENT DOCUMENTS

| WO | 2004009091 A1 | 1/2004 |
| WO | 2006009741 A1 | 1/2006 |
| WO | 2009024550 A1 | 2/2009 |

OTHER PUBLICATIONS

Bradley et al. Drug Discovery Today, pp. 97-103 (2005).*
Cao et al. J.Biol. Chem. vol. 278, pp. 1131-1136 (2003).*
Geyeregger et al. Cell Mol.Life Sci. vol. 63, pp. 524-539 (2006).*
Groot, Journal of Lipid Research, vol. 45, pp. 2182-2191 (2005).*
Hu et al. J.Med. Chem. 49, pp. 6151-6154 (2006).*
Bennett; et al., "An update on non-steroidal liver X receptor agonists and their potential use in the treatment of atherosclerosis", Expert Opinion on Therapeutic Patents, vol. 16, pp. 1673-1699, (2006), Informa Healthcare, Great Britian.

* cited by examiner

*Primary Examiner* — Emily Bernhardt
(74) *Attorney, Agent, or Firm* — James L. McGinnis; Catherine D. Fitch

(57) ABSTRACT

The present invention relates to 1-(4-ureidobenzoyl)piperazine derivatives having the general Formula I (We bring to your attention that formula I is not provided on this electronic version as it is provided in the abstract of the paper copy) Wherein $R_1$ is $(C_{1-8})$alkyl, $(C_{3-8})$cycloalkyl or $(C_{3-8})$cycloalkyl$(C_{1-3})$alkyl, each of which may be substituted by hydroxy, cyano or halogen; $R_2$ represents 1 or 2 optional halogens; $R_3$ is $(C_{1-6})$alkyl, $(C_{3-6})$cycloalkyl or $(C_{3-6})$cycloalkyl$(C_{1-3})$alkyl, each of which may be substituted by one or more halogens; A represents a heteroaryl ring system comprising 1-3 heteroatoms selected from N, O and S, which ring system is 5- or 6-membered when X is C, and 5-membered when X is N; n is 1 or 2; or a pharmaceutically acceptable salt thereof; to pharmaceutical compositions comprising the same, and to the use of a these 1-(4-ureidobenzoyl)piperazine derivatives for the manufacture of a medicament for treating or preventing atherosclerosis and related disorders associated with cholesterol and bile acids transport and metabolism.

(I)

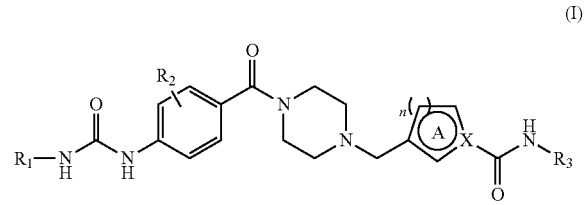

9 Claims, No Drawings

1-(4-UREIDOBENZOYL)PIPERAZINE DERIVATIVES

CROSS REFERENCE TO RELATED APPLICATION

This application is entered into national stage examination under 37 U.S.C. 371 and stems from international patent application No. PCT/US2009/055035 filed on Aug. 26, 2009, which claims priority to U.S. provisional application No. 61/092,469 filed Aug. 28, 2008.

The present invention relates to 1-(4-ureidobenzoyl)piperazine derivatives, to pharmaceutical compositions comprising the same and to the use of these 1-(4-ureidobenzoyl) piperazine derivatives in the treatment of atherosclerosis.

The Liver X Receptors (LXRs) are a family of nuclear receptors that are activated upon binding of the naturally occurring oxysterols inducing transcription of target genes. Two subtypes of LXR (α and β) have been identified and exhibit 77% homology of both their ligand- and DNA-binding domains. Both subtypes are highly conserved between humans and rodents however their tissue expression patterns differ significantly. The expression of LXRα is restricted to tissues involved in lipid metabolism with highest expression in the liver; there are also significant levels in kidney, spleen, small intestine and adipose tissue. LXRβ is very widely distributed and has been found in virtually every tissue examined, including liver and brain. Both LXRα and LXRβ are expressed in macrophages. See Costet et al., *J. Biol. Chem.* 275:28240-28245 (2000).

The roles of the LXR receptors are not fully understood, however LXR is well established as a master regulator of lipid metabolism in the liver and peripheral tissues, and as the key inducer of the ATP-binding cassette transporter A1 (ABCA1) gene (Venkateswaran et al., *Proc. Natl. Acad. Sci. USA.* 97:12097-12102 (2000)).

In the human population, mutations of the ABCA1 gene lead to highly atherogenic lipoprotein profiles (Singaraja et al., *Arterioscler Thromb. Vasc. Biol.* 23:1322-1332 (2003)) which in the most severe form cause Tangier's Disease and associated premature atherosclerosis, (see Bodzioch et al., *Nat. Genet.* 22:347-351 (1999) and Rust et al., *Nat. Genet.* 22:352-355 (1999)). This rare inherited disorder is characterised by very low levels of high density lipoproteins (HDL), macrophage accumulation of cholesterol esters and significantly increased risk of atherosclerotic disease (Brooks-Wilson et al., *Nat. Genet.* 22:336-345 (1999)).

Evidence has demonstrated that up-regulation of ABCA1 in human macrophages and enterocytes of the small intestine, is mediated by LXR activation (Costet et al., supra). Furthermore, LXR agonists have also been shown to promote cholesterol efflux. See Claudel et al., *Proc. Natl. Acad. Sci. USA.* 98:2610-2615 (2001). LXR receptors therefore play a critical role in cholesterol homeostasis in macrophages, and suppression within the local environment of the advanced atherosclerotic plaque may be a key feature of the pathology of the disease.

The potential utility of LXR agonists in the treatment of atherosclerosis has been increasingly documented over the last few years. See for example Levin et al., *Arterioscler. Thromb. Vasc. Biol.* 25:135-142 (2005). Atherosclerosis is a disease of the arteries that exists for many years without causing symptoms. Advanced atherosclerotic plaques can however become vulnerable to rupture, promoting acute thrombosis and clinical events such as myocardial infarction (MI) and stroke. The primary cell type implicated in rupture of atherosclerotic plaques, and subsequent clinical events, is the macrophage.

The primary mechanism for achieving efficacy in atherosclerosis with an LXR agonist is expected to occur by lowering the cholesterol burden of arteries (via upregulation of ABCA1), to generate more stable lesions and thus reduce the clinical events. Additionally, LXR agonists may increase circulating HDL levels due to the role of ABCA1 in generation of nascent HDL by the liver. There is potential for further anti-atherosclerotic effects of LXR agonists due to suppression of inflammation (Joseph et al., *Nat. Med.* 9:213-219 (2003)) and effects on glucose metabolism. See Latiffe et al., *Proc. Natl. Acad. Sci. USA.* 100:5419-24 (2003).

There is a remaining need for compounds that are effective as LXR modulators.

To this aim the present invention provides 1-(4-ureidobenzoyl)piperazine derivatives having the general formula I

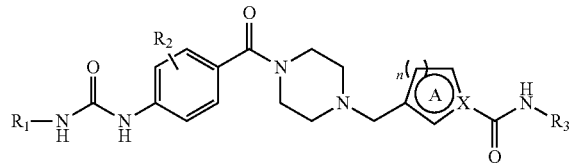

Formula I wherein
$R_1$ is $(C_{1-8})$alkyl, $(C_{3-8})$cycloalkyl or $(C_{1-3})$cycloalkyl$(C_{1-3})$ alkyl, each of which may be substituted by hydroxy, cyano or halogen;
$R_2$ represents 1 or 2 optional halogens;
$R_3$ is $(C_{1-6})$alkyl, $(C_{3-6})$cycloalkyl or $(C_{3-6})$cycloalkyl$(C_{1-3})$ alkyl, each of which may be substituted by one or more halogens;
A represents a heteroaryl ring system comprising 1-3 heteroatoms selected from N,
O and S, which ring system is 5- or 6-membered when X is C, and 5-membered when
X is N; n is 1 or 2; or a pharmaceutically acceptable salt thereof.

The term $(C_{1-8})$alkyl as used in the definition of Formula I means a branched or unbranched alkyl group having 1-8 carbon atoms, like octyl, hexyl, pentyl, isopentyl, butyl, isobutyl, tertiary butyl, propyl, isopropyl, ethyl and methyl.

The term $(C_{1-6})$alkyl as used in the definition of Formula I means a branched or unbranched alkyl group having 1-6 carbon atoms, like hexyl, pentyl, butyl, isobutyl, tertiary butyl, propyl, isopropyl, ethyl and methyl.

Likewise, the term $(C_{1-3})$alkyl used in the definition of Formula I means a branched or unbranched alkyl group having 1-3 carbon atoms, like propyl, isopropyl, ethyl and methyl.

The term $(C_{3-8})$cycloalkyl means a cycloalkyl group having 3-8 carbon atoms, like cycloheptyl, cyclohexyl, cyclopentyl, cyclobutyl and cyclopropyl.

The term $(C_{3-8})$cycloalkyl$(C_{1-3})$alkyl means a $(C_{1-3})$alkyl group, having the meaning as defined above, substituted with a $(C_{3-8})$cycloalkyl group, having the meaning as defined above. Examples are cyclopropylmethyl, cyclobutylmethyl, 2-cyclopropylethyl, 2-cyclobutylethyl and the like. A preferred $(C_{3-8})$cycloalkyl$(C_{1-3})$alkyl is cyclopropyl-methyl.

The term a 5- or 6-membered heteroaryl ring system A comprising 1-3 heteroatoms selected from N, O and S, means a 1,3-diradical heteroarylene group derived from heteroaromatic rings such as exemplified by oxazole, isoxazole, oxadiazole, thiadiazole, furan, pyrrole, pyrazole, pyrazine, pyridinel, pyrimidine, imidazole, thiazole, thiadiazole, thiophene and the like. Examples of such 5-membered heteroarylene are oxazol-2,4-diyl, isoxazol-3,5-diyl, thiazol-2,4-diyl, furan-2,5,-diyl, thiophen-2,5-diyl, pyrazol-1,3-diyl, pyrrol-1,3-diyl, imidazol-1,4-diyl, tetrazol-2,5-diyl, [1,2,4] oxadiazol-3,5-diyl and the like. Examples of 6-membered heteroarylene are pyridine-2,4-diyl, pyridine-2,6-diyl, pyrimidin-2,4-diyl, pyridazin-3,5-diyl, pyrazine-2,6-diyl and the like.

The term halogen means F, Cl, Br or I. Preferred are F and Cl.

There is a preference for 1-(4-ureidobenzoyl)piperazine derivatives of formula I wherein A represents furan-2,5,diyl or pyridine-2,6-diyl.

Further preferred are the 1-(4-ureidobenzoyl)piperazine derivatives of formula I, wherein in addition $R_2$ represents 1 or 2 halogens selected from F and Cl.

More preferred are the 1-(4-ureidobenzoyl)piperazine derivatives of formula I wherein in addition $R_3$ is tert-butyl.

Particular 1-(4-ureidobenzoyl)piperazine derivatives of the invention are:

N-tert-butyl-5-((4-(4-(3-cyclobutylureido)-3-fluorobenzoyl)piperazin-1-yl)methyl)furan-2-carboxamide;
N-tert-butyl-5-((4-(3-fluoro-4-(3-isobutylureido)benzoyl)piperazin-1-yl)methyl)furan-2-carboxamide;
N-tert-butyl-5-((4-(4-(3-(cyclopropylmethyl)ureido)-3-fluorobenzoyl)piperazin-1-yl)methyl)furan-2-carboxamide;
N-tert-butyl-5-((4-(3-fluoro-4-(3-neopentylureido)benzoyl)piperazin-1-yl)methyl)furan-2-carboxamide;
N-tert-butyl-5-((4-(3-fluoro-4-(3-isopentylureido)benzoyl)piperazin-1-yl)methyl)furan-2-carboxamide;
N-tert-butyl-5-((4-(4-(3-butylureido)-3-fluorobenzoyl)piperazin-1-yl)methyl)furan-2-carboxamide hydrochloride;
N-tert-butyl-5-((4-(3-chloro-4-(3-neopentylureido)benzoyl)piperazin-1-yl)methyl)furan-2-carboxamide;
N-tert-butyl-5-((4-(3-chloro-4-(3-isobutylureido)benzoyl)piperazin-1-yl)methyl)furan-2-carboxamide;
N-tert-butyl-5-((4-(3-chloro-4-(3-(cyclopropylmethyl)ureido)benzoyl)piperazin-1-yl)methyl)furan-2-carboxamide;
N-tert-butyl-5-((4-(3-chloro-4-cyclobutylureido)benzoyl)piperazin-1-yl)methyl)furan-2-carboxamide;
N-tert-butyl-5-((4-(3-chloro-4-(3-isopentylureido)benzoyl)piperazin-1-yl)methyl)furan-2-carboxamide;
N-tert-butyl-5-((4-(4-(3-butylureido)-3-chlorobenzoyl)piperazin-1-yl)methyl)furan-2-carboxamide;
N-tert-butyl-5-((4-(4-(3-(cyclopropylmethyl)ureido)-2,3-difluorobenzoyl)piperazin-1-yl)methyl)furan-2-carboxamide;
N-tert-butyl-5-((4-(2,3-difluoro-4-(3-neopentylureido)benzoyl)piperazin-1-yl)methyl)furan-2-carboxamide;
N-tert-butyl-5-((4-(2,3-difluoro-4-(3-isobutylureido)benzoyl)piperazin-1-yl)methyl)furan-2-carboxamide;
N-tert-butyl-5-((4-(4-(3-cyclobutylureido)-2,3-difluorobenzoyl)piperazin-1-yl)methyl)furan-2-carboxamide;
N-tert-butyl-5-((4-(4-(3-butylureido)-2,3-difluorobenzoyl)piperazin-1-yl)methyl)furan-2-carboxamide;
N-tert-butyl-5-((4-(2,3-difluoro-4-(3-isopentylureido)benzoyl)piperazin-1-yl)methyl)furan-2-carboxamide;
N-tert-butyl-6-((4-(4-(3-cyclobutylureido)-3-fluorobenzoyl)piperazin-1-yl)methyl)picolinamide;
N-tert-butyl-6-((4-(3-fluoro-4-(3-neopentylureido)benzoyl)piperazin-1-yl)methyl)picolinamide;
N-tert-butyl-6-((4-(3-fluoro-4-(3-isopentylureido)benzoyl)piperazin-1-yl)methyl)picolinamide;
N-tert-butyl-6-((4-(4-(3-(cyclopropylmethyl)ureido)-3-fluorobenzoyl)piperazin-1-yl)methyl)picolinamide; or a pharmaceutically acceptable salt thereof.

The 1-(4-ureidobenzoyl)piperazine derivatives of the invention can be prepared using general synthetic methods known in the art of organic synthesis. A synthesis route for the compounds of Formula I wherein X is C is depicted in Scheme 1 and a synthesis route for the compounds of Formula I wherein X is N is depicted in Scheme 2. Those skilled in the art know that the order of addition of the key building blocks according to Formulas 2-13 in Schemes 1 and 2 can be altered and still give the desired products of Formula 1.

Following the route represented by Scheme 1, a piperazine intermediate of Formula 2, wherein Y represents an amino protecting group, such as for example a tert-butyloxycarbonyl group (t-Boc), is alkylated with a heteroaryl ester derivative of Formula 3, wherein alkyl represent a lower alkyl group, preferably methyl, and wherein L represents a leaving group such as chloro, bromo or $OSO_2Me$, in a solvent, e.g. dichloromethane or acetonitrile, at room or elevated temperature using an organic base e.g. triethylamine or inorganic base e.g. potassium carbonate to give an intermediate amino ester derivative of Formula 4.

Ester hydrolysis of the intermediate of Formula 4 using e.g. sodium hydroxide in methanol/water gives an acid or the sodium salt of an acid which can be coupled with an amine of formula $H_2NR_3$, wherein $R_3$ has the meaning as previously defined, in a solvent e.g. dichloromethane using a coupling agent e.g. N-(3-dimethylaminopropyl)-N'-ethylcarbodiimide hydrochloride or 1-propanephosphonic acid cyclic anhydride to give the amide derivative of Formula 5. Deprotection of the Boc-protected piperazine amino function in intermediate of Formula 5, e.g. using trifluoroacetic acid in dichloro-methane, provides the intermediate piperazine derivative of Formula 6, which is subsequently coupled with a benzoic acid derivative of Formula 7, wherein $R_2$ has the meaning as previously defined, in a solvent e.g. dichloromethane using a coupling agent e.g. N-(3-dimethylaminopropyl)-N'-ethylcarbodiimide hydrochloride or 1-propanephosphonic acid cyclic anhydride, to give the aniline intermediate of Formula 8. Activation of this aniline intermediate by reaction with 4-nitrophenylchoroformate or with (bis(trichloromethyl)carbonate (triphosgene) in a solvent e.g. dichloromethane at room or elevated temperature, followed by reaction with an amine of Formula $R_1NH_2$, wherein $R_1$ has the meaning as previously defined, in the presence of a base e.g. triethylamine or N,N-diisopropylethylamine produces a 1-(4-ureidobenzoyl)piperazine derivative of the invention according to Formula I.

Scheme 1

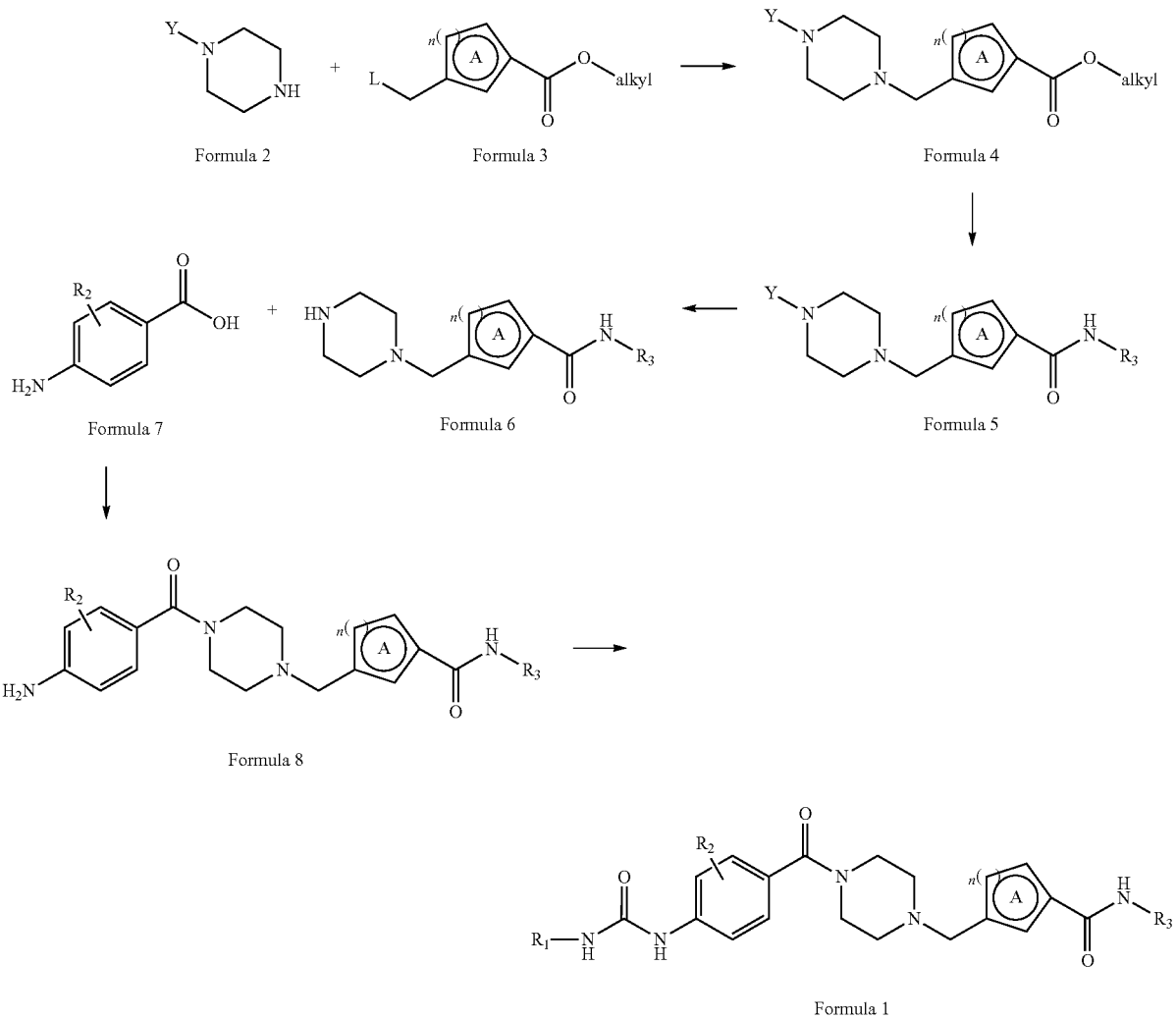

Formula 9 is reacted with an isocyanate of formula $R_3$—NCO, wherein $R_3$ has the meaning as previously defined, in a solvent e.g. dichloromethane at room or elevated temperature to give the urea derivative of Formula 10. Activation of the aromatic methyl substituent by bromination using N-bromosuccinimide and benzoyl peroxide in carbon tetrachloride at room or elevated temperatures provides the intermediate urea derivative of Formula 11 where the leaving group L is bromine.

Alkylation of a piperazine derivative of Formula 2, wherein Y is a N-protecting group, such as for example a tert-butyloxycarbonyl group (t-Boc), with a urea derivative of Formula 11, in a solvent e.g. dichloromethane or acetonitrile at room or elevated temperature using an organic base e.g. triethylamine or inorganic base e.g. potassium carbonate, followed by the deprotection of the Boc-group e.g. using trifluoroacetic acid and dichloromethane, provides the piperazine derivative of Formula 12.

Scheme 2

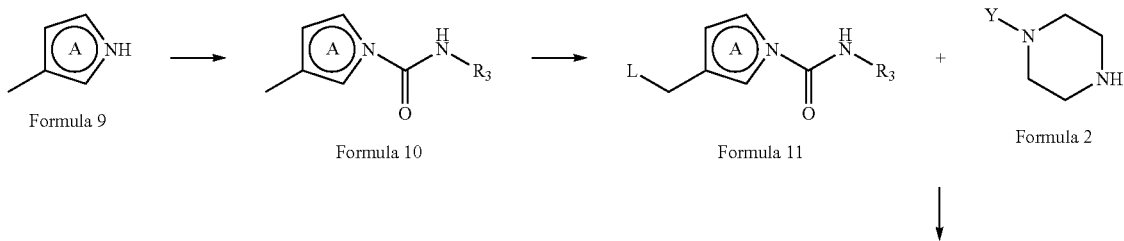

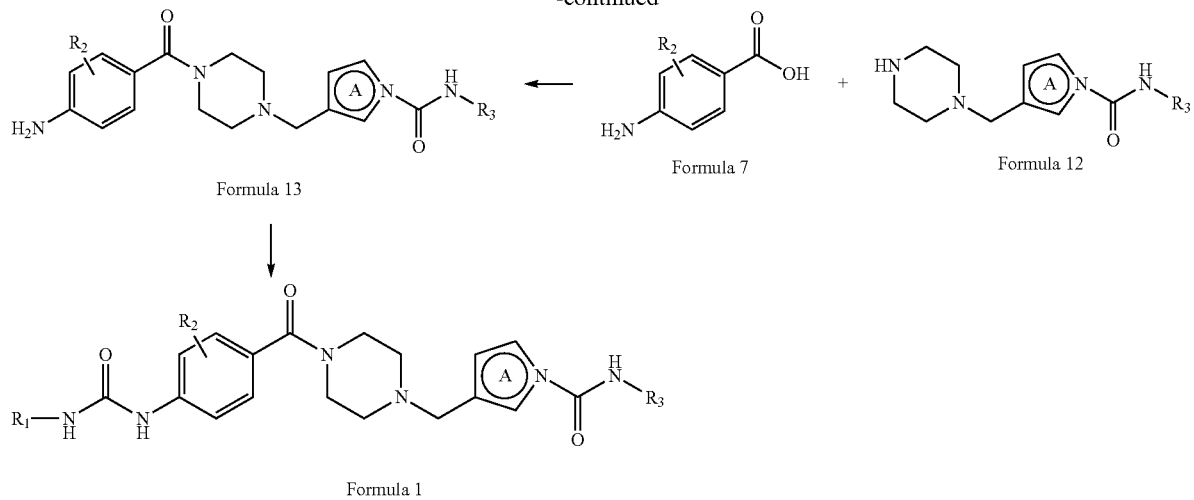

Formula 13            Formula 7            Formula 12

Formula 1

Reaction of a piperazine derivative of Formula 12, with a benzoic acid derivative of Formula 7, wherein $R_2$ has the meaning as previously defined, in a solvent e.g. dichloromethane with the aid of a coupling agent e.g. N-(3-dimethylaminopropyl)-N'-ethylcarbodiimide hydrochloride or 1-propanephosphonic acid cyclic anhydride, gives the aniline intermediate of Formula 13. 1-(4-Ureidobenzoyl)piperazine derivatives of the invention according to Formula I, wherein X is N, can be prepared from the intermediates of Formula 13 by reaction with 4-nitrophenylchoroformate or with (bis (trichloromethyl)carbonate (triphosgene) in a solvent e.g. dichloromethane at room or elevated temperature, followed by addition of the desired amine of Formula $R_1NH_2$, wherein $R_1$ has the meaning as previously defined, in the presence of a base e.g. triethylamine or N,N-diisopropylethylamine.

The piperazine derivatives of Formula 2, the ester derivatives of Formula 3, the 4-aminobenzoic acid derivatives of Formula 7, as well as the methylated heteroaryl derivatives of Formula 9 can be prepared using methods well known in the art from commercially available intermediates.

The term N-protecting group, as used above, means a group commonly used for the protection of an amino group, like the alloxycarbonyl (Alloc) group, the tert-butyloxycarbonyl (Boc) group, the benzyloxycarbonyl (Z) group or the 9-fluorenylmethyloxycarbonyl (Fmoc) group. Removal of these and other protecting groups can take place in different ways, depending on the nature of those protecting groups. An overview of protecting groups and methods for their removal is given in T. W. Greene and P. G. M. Wuts, "*Protective Groups in Organic Synthesis*", $2^{nd}$ edition, 1991, John Wiley & Sons, Inc.

The 1-(4-ureidobenzoyl)piperazine derivatives of Formula I and their salts may contain at least one centre of chirality, and can exist therefore as stereoisomers, including enantiomers and diastereomers. The present invention includes the aforementioned stereoisomers within its scope and each of the individual R and S enantiomers of the compounds of Formula I and their salts, substantially free, i.e. associated with less than 5%, preferably less than 2%, in particular less than 1% of the other enantiomer, and mixtures of such enantiomers in any proportions including the racemic mixtures containing substantially equal amounts of the two enantiomers. Methods for asymmetric synthesis whereby the pure stereoisomers are obtained are well known in the art, e.g. synthesis with chiral induction or starting from chiral intermediates, enantioselective enzymatic conversions, separation of stereoisomers or enantiomers using chromatography on chiral media. Such methods are for example described in *Chirality in Industry* (edited by A. N. Collins, G. N. Sheldrake and J. Crosby, 1992; John Wiley).

In a further aspect of the invention the 1-(4-ureidobenzoyl) piperazine derivatives of Formula I and their salts may contain 1 or more non-natural isotopes in any of the structural positions. Such isotope-labeled compounds of the invention can for instance be used in in vivo studies on their absorption, distribution, metabolism and excretion (ADME). Isotopes include radioisotopes such as tritium or $^{14}C$. Alternatively, compounds may also be enriched with stable isotopes such as deuterium, $^{13}C$, $^{18}O$ or $^{15}N$. $^{11}C$ and $^{18}F$ are the preferred isotopes to be incorporated in a compound of the invention for use as a PET (Positron Emission Tomography) tracer.

Pharmaceutically acceptable salts may be obtained by treating a free base of a 1-(4-ureidobenzoyl)piperazine derivative of Formula I with a mineral acid such as hydrochloric acid, hydrobromic acid, phosphoric acid and sulfuric acid, or an organic acid such as for example ascorbic acid, citric acid, tartaric acid, acetic acid, maleic acid, malonic acid, fumaric acid, glycolic acid, succinic acid, propionic acid, acetic acid, methane sulfonic acid, and the like.

The compounds of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a 1-(4-ureidobenzoyl)piperazine derivative having the general Formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition, Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For par-enteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The 1-(4-ureidobenzoyl)piperazine derivatives of the present invention were found to be modulators of LXRα and/or LXRβ, especially having agonistic activity thereon, and are as such useful in preventing and reducing the risk of atherosclerosis and related disorders associated with cholesterol and bile acids transport and metabolism, such as hypercholesterolemia (e.g. coronary heart disease), cholesterol gallstones, lipid storage diseases, diabetes and obesity.

The compounds of the invention are potentially also useful in further indications such as:

Inflammatory Disease

Ligand activation of LXR has been shown to inhibit a number of inflammatory pathways e.g. Interleukin1-β, Interleukin-6, cyclooxygenase-2 and most recently shown to directly inhibit C-reactive protein expression. See Blaschke et al., *Circ. Res.* 99: 88-99. (2006). Compounds of the invention may have therapeutic utility in suppression of inflammation in inflammatory diseases such as contact dermatitis (see Fowler et al., *J. Invest. Dermatol.* 120:246-55. (2003); neuroinflammatory diseases such as multiple sclerosis (Zhang-Gandhi and Drew. *J. Neuroimmuno* 183:50-59. (2007)) and autoimmune encephalomyelitis. See Hindinger et al., *J. Neurosci Res.* 84:1225-1234 (2006).

Proliferative Vascular Disease

The LXR ligand T0901317 has been shown to inhibit vascular smooth muscle cell proliferation and neointima formation following balloon injury in vitro and in vivo. Compounds of the invention may therefore have therapeutic utility in proliferative vascular diseases. See Blaschke et al., *Circ. Res.* 95:110-123 (2004).

Diabetes/Metabolic Syndrome

Recent literature has demonstrated efficacy of LXR agonists in animal models of insulin resistance and diabetes and thus compounds of the invention may have potential therapeutic utility in the treatment of diabetes and metabolic syndrome (see Liu et al., *Endocrinology.* 147:5061-5068 (2006); Fernandez-Veledo et al, *Diabetologia.* 49:3038-3048 (2006)).

Cancer

The LXR agonist T0901317 delayed progression of tumours in an animal model of prostate cancer. Compounds of the invention may be potentially useful for treatment of prostate cancer. See Chuu et al., *Cancer. Res.* 66:6482-6486 (2006).

Neurodegenerative Disease

Via modulation of cellular cholesterol levels, LXR agonists can reduce the deposition of β-amyloid in the brain. In addition T0901317 has been shown to lower deposition of β-amyloid but also improve memory. See Riddell et al., *Mol. Cell. Neurosci.* 34: 621-628 (2007). The agonist derivatives of the present invention may therefore have therapeutic utility in neurodegenerative diseases such as Alzheimers disease.

Combination Therapies

The compounds of the invention may be combined with another therapeutic agent that is useful in the treatment of other metabolic disorders such as; hypertension, hyperlipidaemias, dyslipidaemias, diabetes, chronic inflammatory disorders, obesity and in any condition where enhancement of reverse cholesterol transport and/or improvement of LDL: HDL ratios would be of potential clinical benefit. Examples of such therapies are: inhibitors of 3-hydroxy-3-methyl-glutaryl-CoA reductase (HMG CoA reductase) (e.g. atorvastatin, pravastatin, simvastatin, lovastatin, rosuvastatin and others), cholesterol absorption inhibitors (e.g. ezetimibe), bile sequestrants (e.g. cholestyramine), microsomal triglyceride transfer protein (MTP) inhibitors, peroxisome proliferator-activated receptor modulators (e.g. muraglitazar, rosiglitazone, fibrates and others), cholesterol ester transfer protein inhibitors, nicotinic acid derivatives (e.g. Niaspan® etc), Acyl coenzyme A: cholesterol acyl transferase (ACAT) inhibitors (e.g. eflucimibe), farnesoid X receptor modulators, therapies used for the treatment of metabolic syndrome or type 2 diabetes e.g. metformin. Compounds of the invention may be combined with anti-inflammatory therapies (e.g. aspirin) and with treatments for neurodegenerative diseases (e.g Aricept®, Exelon®, Reminyl® and Ebixa®).

The compounds of the invention may be administered for humans in a sufficient amount and for a sufficient amount of time to alleviate the symptoms. Illustratively, daily dosage levels for humans can be in the range of 0.001-50 mg per kg body weight, preferably in a daily dosage of 0.01-20 mg per kg body weight.

The invention is illustrated by the following Examples.

GENERAL EXPERIMENTAL

High Performance Liquid Chromatography (HPLC)

HPLC purification is used within this experimental section and refers to High Performance Liquid Chromatography. Some examples of general methods that may be used to purify compounds are: acidic reverse phase HPLC (water/acetonitrile/0.1% trifluoroacetic acid) using a standard gradient of 5% acetonitrile/95% water to 100% acetonitrile or basic reverse phase HPLC (water/acetonitrile/0.1% ammonia solution) using a standard gradient of 10% acetonitrile/90% water to 100% acetonitrile. UV detection e.g. 254 nM is used for the collection of fractions from HPLC. This description gives general methods and variations in types of equipment, columns, mobile phase, detection wavelength, solvent gradient and run time may also be used to purify compounds.

Free Base and Salts

After purification by acidic HPLC basic products can either be isolated as the trifluoroacetic acid salt or liberated as the free base by common generic methods e.g. strong cation exchange chromatography eluting with 2M ammonia in methanol or silica carbonate column chromatography or partitioning between an organic solvent e.g. ethyl acetate and aqueous base e.g. sodium hydrogen carbonate, separating the organic layer, drying with inorganic solid e.g. magnesium sulfate, filtering and concentration under reduced pressure.

The free base of products can also be converted to hydrochloride salts by standard methods e.g. dissolving the free base in dichloromethane and adding 2M hydrochloric acid in ether and concentrating under reduced pressure to give the hydrochloride salt.

ABBREVIATIONS

Boc: tert-butoxycarbonyl; CDCl$_3$: chloroform-d; CD$_3$OD: methanol-d4; (CD$_3$)$_2$SO: dimethylsulfoxide-d6; HPLC: high performance liquid chromatography; HATU: O-(7-azabenzotriazol-1-yl)-N,N,N,N-tetramethyl uronium hexafluorophosphate; SCX: strong cation exchange; triphosgene: (bis(trichloromethyl)carbonate.

Example 1

N-tert-Butyl-2-((4-(4-(3-cyclobutylureido)benzo) piperazin-1-yl)methyl)oxazole-4-carboxamide 2,2,2-trifluoroacetate

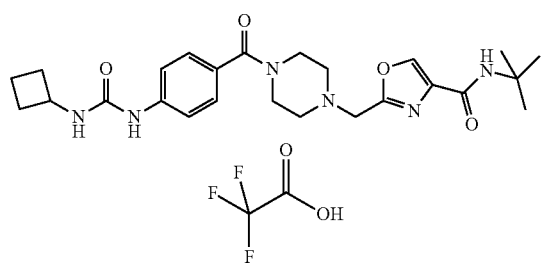

A: Methyl 2-(piperazin-1-ylmethyl)oxazole-4-carboxylate 2,2,2-trifluoroacetate

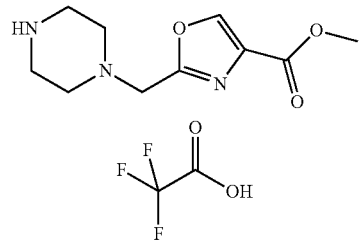

A dimethyl sulfoxide (10 mL) solution of tert-butyl-1-piperazine carboxylate (1.06 g, 5.70 mmol) and N,N-diisopropylethylamine (2.98 mL, 17.1 mmol) was treated at room temperature with methyl (2-chloromethyl)oxazole-4-carboxylate (1.0 g, 5.70 mmol; portion-wise addition) and stirred overnight. The mixture was diluted with ethyl acetate and washed with saturated aqueous sodium chloride. The organic layer was dried on magnesium sulfate, filtered and concentrated to give the intermediate tert-butyl 4-((4-(methoxycarbonyl)oxazol-2-yl)methyl)piperazine-1-carboxylate (MS (ESI) m/z 325.7 [M+H]$^+$. The intermediate was dissolved in dichloromethane (15 mL) at room temperature and treated with trifluoroacetic acid (5 mL) dropwise. The mixture was stirred for 4 hours and was then concentrated under vacuum to give the title compound (1.60 g). MS (ESI) m/z 226.1 [M+H]$^+$.

B: Ethyl 4-(3-cyclobutylureido)benzoate

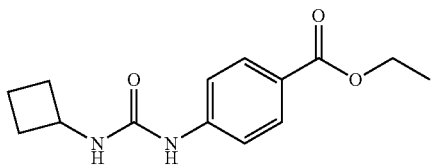 [SMILES: CCOC(=O)c1ccc(NC(=O)NC2CCC2)cc1]

Cyclobutylamine (27.91 g, 392.4 mmol, 33.5 mL) was added dropwise to a stirred solution of ethyl 4-isocyanatobenzoate (25 g, 130.8 mmol) in dichloromethane. After 40 minutes stirring, the solid precipitate that had formed was filtered off and dried to afford the title compound (30.28 g). MS (ESI) m/z 263.1 [M+H]$^+$ C: 4-(3-Cyclobutylureido)benzoic acid Ethyl 4-(3-cyclobutylureido)benzoate (49.9 mmol, 13.1 g) was suspended in ethanol (400 ml) and treated with 4M sodium hydroxide (300 mmol, 74.9 ml). The mixture was then stirred at reflux for 18 hours. The reaction was allowed to cool, diluted with toluene (100 mL) and concentrated under vacuum. Acidification to pH 3 with 5M aqueous hydrochloric acid produced a white solid. The solid was collected by vacuum filtration, washed with cold ethanol and dried under vacuum to give the title compound as a white powder (11.0 g).

¹H NMR (CD₃OD, 400 MHz): δ 1.73 (2H, m), 1.92 (2H, m), 2.32 (2H, m), 4.22 (1H, m), 7.45 (2H, d), 7.90 (2H, d)

D: Methyl 2-((4-(4-(3-cyclobutylureido)benzoyl)piperazin-1-yl)methyl)oxazole-4-carboxylate

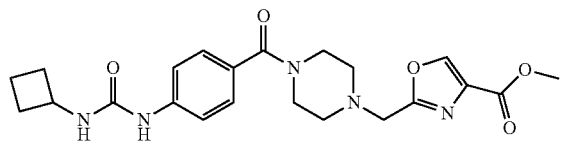 [SMILES: COC(=O)c1coc(CN2CCN(C(=O)c3ccc(NC(=O)NC4CCC4)cc3)CC2)n1]

To a N,N-dimethylformamide (3 mL) solution of methyl 2-(piperazin-1-yl-methyl)oxazole-4-carboxylate 2,2,2-trifluoroacetate (174 mg, 513 µmol) and 4-(3-cyclobutylureido)benzoic acid (120 mg, 513 µmol) in N,N-dimethylformamide (5 mL) was added N,N-diisopropylethylamine (357 µL, 2.05 mmol), followed by O-(7-azabenzotriazol-1-yl)-N,N,N,N-tetramethyl uronium hexafluorophosphate (293 mg, 770 µmol; HATU). The mixture was stirred at room temperature for 22 hours and was then concentrated under vacuum. The residue was taken up in ethyl acetate and washed with saturated aqueous ammonium chloride and brine. The organic phase was dried on magnesium sulfate, filtered and concentrated under vacuum. The crude residue was applied to a silica gel column and eluted with 25% ethyl acetate in n-hexanes to give the title compound (34 mg). MS (ESI) m/z 442.1 [M+H]⁺

E: 2-((4-(4-(3-Cyclobutylureido)benzoyl)piperazin-1-yl)methyl)oxazole-4-carboxylic acid 2,2,2-trifluoroacetate Methyl 2-((4-(4-(3-cyclobutylureido)benzoyl)piperazin-1-yl)methyl)oxazole-4-carboxylate (30 mg, 68 µmol) was dissolved in a mixture of methanol/water (5:1; 3 mL) at room temperature. Lithium hydroxide (20 mg, 477 µmol; monohydrate) was added, and the mixture was stirred for 1 hour. The mixture was concentrated to near dryness, diluted with water (2 mL) and brought to pH 2-3 by addition of concentrated hydrochloric acid. The crude solution was purified by acidic reverse phase HPLC to give the title compound (32 mg) MS (ESI) m/z 428.1 [M+H]⁺

F: 1-(4-(1-((4-(tert-Butylcarbamoyl)oxazol-2-yl)methyl)piperazine-4-carbonyl)phenyl) 3-cyclobutylurea 2,2,2-trifluoroacetate To a solution of 2-((4-(4-(3-cyclobutylureido)benzoyl)piperazin-1-yl)methyl)-oxazole-4-carboxylic acid 2,2,2-trifluoroacetate (8 mg, 15 µmol) in N,N-dimethyl-acetamide (1 mL) was added O-(7-azabenzotriazol-1-yl)-N,N,N,N-tetramethyl uronium hexafluorophosphate (5.7 mg, 154 µmol; HATU), tert-butylamine (1.6 µL, 15 µmol) and N,N-diisopropylethylamine (3.9 µL, 23 µmol). The reaction mixture was stirred at room temperature for 20 hours and was then concentrated under vacuum. The crude residue was purified by acidic reverse phase HPLC to give the title compound (5.6 mg). MS (ESI) m/z 483.1 [M+H]⁺

The following compounds were prepared in a similar manner:

1B: N-Cyclobutyl-2-((4-(4-(3-cyclobutylureido)benzoyl)piperazin-1-yl)methyl)oxazole-4-carboxamide
MS (ESI) m/z 481.1 [M+H]⁺

1C: N-sec-Butyl-2-((4-(4-(3-cyclobutylureido)benzoylpiperazin-1-yl)methyl)oxazole-4-carboxamide 2,2,2-trifluoroacetate, racemate
MS (ESI) m/z 483.1 [M+H]⁺.

1D: 2-((4-(4-(3-Cyclobutylureido)benzoyl)piperazin-1-yl)methyl)-N-cyclopentyl-oxazole-4-carboxamide 2,2,2-trifluoroacetate
MS (ESI) m/z 495.1 [M+H]⁺.

Example 2

N-tert-Butyl-2-((4-(4-(3-cyclopropyl methyl)ureido)-3-fluorobenzoyl)piperazin-1-yl)methyl)thiazole-4-carboxamide

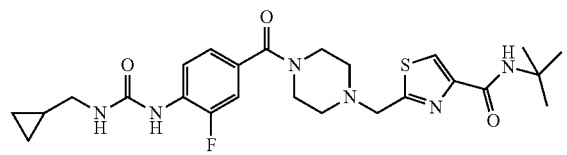 [SMILES: CC(C)(C)NC(=O)c1csc(CN2CCN(C(=O)c3ccc(NC(=O)NCC4CC4)c(F)c3)CC2)n1]

A: Ethyl 2-((4-(tert-butoxycarbonyl)piperazin-1-yl)methyl)thiazole-4-carboxylate

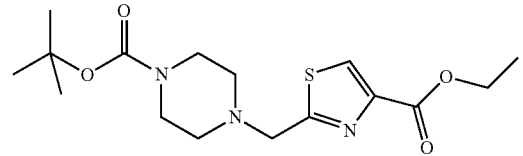 [SMILES: CCOC(=O)c1csc(CN2CCN(C(=O)OC(C)(C)C)CC2)n1]

tert-Butyl 1-piperazinecarboxylate (1.811 g, 9.72 mmol), 2-chloromethyl-thiazole-4-carboxylic acid ethyl ester (2 g, 9.72 mmol), potassium carbonate (2.69 g, 19.45 mmol) and sodium iodide (0.292 g, 1.945 mmol) were combined and stirred in acetonitrile at reflux for 2 hours. The reaction was concentrated under reduced pressure. The residue was taken up in dichloromethane and filtered. The filtrate was concentrated under reduced pressure to give the title compound (4.38 g).
MS (ESI) m/z 356.5 [M+H]⁺

B: Sodium 2-((4-(tert-4-tert-butoxycarbonyl)piperzin-1-yl)methyl)thiazole-4-carboxylate

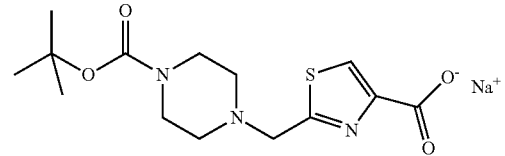 [SMILES: CC(C)(C)OC(=O)N1CCN(Cc2nc(C(=O)[O-])cs2)CC1 ; [Na+]]

Ethyl 2-((4-(tert-butoxycarbonyl)piperazin-1-yl)methyl) thiazole-4-carboxylate (4.3871 g, 12.34 mmol) and sodium hydroxide (0.494 g, 12.34 mmol) were combined and stirred in ethanol at reflux for 3 hours. The reaction was concentrated under reduced pressure to afford the title compound (3.56 g). MS (ESI) m/z 328.3 [M+H]+

C: tert-Butyl 4-((4-(tert-butylcarbamoyl)thiazol-2-yl) methyl)piperazine-1-carboxylate

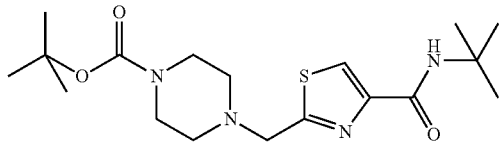 [SMILES: CC(C)(C)NC(=O)c1csc(CN2CCN(C(=O)OC(C)(C)C)CC2)n1]

To a solution of sodium 2-((4-(tert-butoxycarbonyl)piperazin-1-yl)methyl)-thiazole-4-carboxylate (3.596 g, 10.29 mmol), tert butylamine (0.753 g, 10.29 mmol, 1.082 mL) and triethylamine (3.12 g, 30.9 mmol, 4.29 mL) in dichloromethane (50 mL) was added 1-propanephosphonic acid cyclic anhydride (13.10 g, 20.58 mmol, 12.25 mL, 50% solution in ethyl acetate. The reaction was concentrated under reduced pressure and the residue was taken up in ethyl acetate, washed with sodium bicarbonate (×3) and brine. The organic phase was concentrated under reduced pressure to afford the title compound (2.10 g). MS (ESI) m/z 283.5 [M+H]+

D: N-tert-Butyl-2-(piperazin-1-ylmethyl)thiazole-4-carboxamide

Tert-butyl 4-((4-(tert-butylcarbamoyl)thiazol-2-yl)methyl)piperazine-1-carboxylate (2.1 g, 5.49 mmol) was dissolved in dichloromethane (20 mL). 2,2,2-Trifluoroacetic acid (20 mL) was added and the reaction mixture was stirred for 2 hours. The reaction was concentrated under reduced pressure and purified by SCX column chromatography to give the title compound (1.28 g). MS (ESI) m/z 283.4 [M+H]+

E: 2-((4-(4-Amino-3-fluorobenzoyl)piperazin-1-yl) methyl)-N-tert-butylthiazole-4-carboxamide

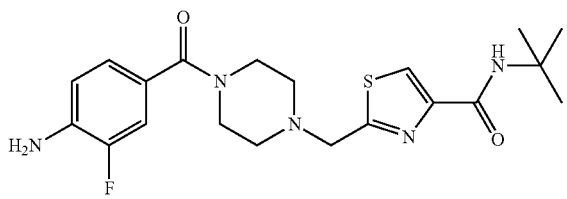 [SMILES: CC(C)(C)NC(=O)c1csc(CN2CCN(C(=O)c3ccc(N)c(F)c3)CC2)n1]

To a solution of 4-amino-3-fluorobenzoic acid (0.703 g, 4.53 mmol), N-tert-butyl-2-(piperazin-1-ylmethyl)thiazole-4-carboxamide (1.28 g, 4.53 mmol) and triethylamine (0.459 g, 4.53 mmol, 0.630 mL) in dichloromethane was added 1-propanephosphonic acid cyclic anhydride (2.88 g, 4.53 mmol, 2.70 mL, 50% solution in ethyl acetate). The reaction was concentrated under reduced pressure and the residue was taken up in ethyl acetate, washed with sodium bicarbonate (×3) and brine. The organic phase was concentrated under reduced pressure to afford the title compound (0.87 g). MS (ESI) m/z 420.3 [M+H]+

F: N-tert-Butyl-2-((4-(4-(3-(cyclopropylmethyl)ureido)-3-fluorobenzoyl)piperazin-1-yl)methyl)thiazole-4-carboxamide 2-((4-(4-Amino-3-fluorobenzoyl)piperazin-1-yl)methyl)-N-tert-butylthiazole-4-carboxamide (100 mg, 0.238 mmol) and 4-nitrophenol chloroformate (48 mg, 0.238 mmol) were combined and stirred in dichloromethane for 1 hour at room temperature. Cyclopropylmethylamine (50.9 mg, 0.715 mmol, 62 µl) was added and the reaction was stirred for 30 minutes. The reaction mixture was diluted with water and flushed through a hydrophobic frit. The organic phase was concentrated under vacuum and purified by acidic reverse phase HPLC to afford the title compound (5 mg). MS (ESI) m/z 517.3 [M+H]+

The following compounds were prepared in a similar manner:

2B: N-tert-Butyl-2-((4-(4-(3-cyclobutylureido)benzoyl)piperazin-1-yl)methyl)thiazole-4-carboxamide
MS (ESI) m/z 517.5 [M+H]+

2C: N-tert-Butyl-2-((4-(4-(3-isopentylureido)benzoyl)piperazin-1-yl)methyl)thiazole-4-carboxamide
MS (ESI) m/z 533.5 [M+H]+

Example 3

N-tert-Butyl-5-((4-(4-(3-cyclobutylureido)-3-fluorobenzoyl)piperazin-1-yl)methyl)furan-2-carboxamide

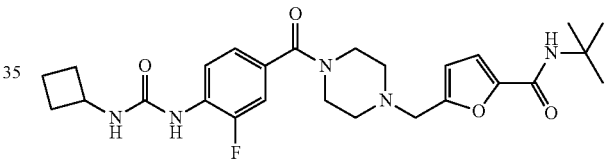

A: Tert-Butyl 4-((5-(methoxycarbonyl)furan-2-yl) methylpiperazine-1-carboxylate

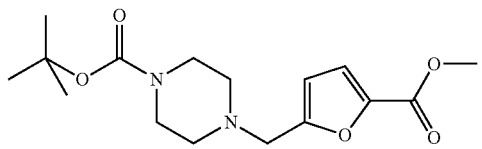 [SMILES: COC(=O)c1ccc(CN2CCN(C(=O)OC(C)(C)C)CC2)o1]

Tert-butyl 1-piperazinecarboxylate (2.134 g, 11.46 mmol), methyl 5-(chloro-methyl)-2-furoate (2 g, 11.46 mmol), potassium carbonate (3.17 g, 22.91 mmol) and sodium iodide (0.343 g, 2.291 mmol) were combined and stirred in acetonitrile at reflux for 2 hours. The reaction was concentrated under reduced pressure. The residue was taken up in dichloromethane and filtered. The filtrate was concentrated under reduced pressure to afford the title compound (4.99 g). MS (ESI) m/z 325.3 [M+H]+

B: Sodium 5-((4-(tert-butoxycarbonyl)piperazin-1-yl)methyl)furan-2-carboxylate

Tert-butyl 4-((5-(methoxycarbonyl)furan-2-yl)methyl) piperazine-1-carboxylate (4.99 g, 15.39 mmol) and sodium hydroxide (0.616 g, 15.39 mmol) were combined and stirred at reflux for 3 hours. The reaction was concentrated under reduced pressure to give the title compound (4.59 g). MS (ESI) m/z 311.4 [M+H]+

C: tert-Butyl 4-((5-(tert-butylcarbamoyl)furan-2-yl)methyl)piperazine-1-carboxylate

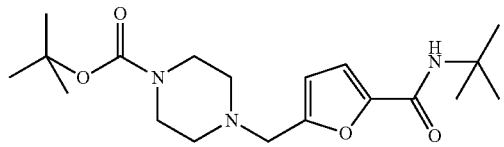 [SMILES: CC(C)(C)NC(=O)c1ccc(CN2CCN(C(=O)OC(C)(C)C)CC2)o1]

To a solution of sodium 5-((4-(tert-butoxycarbonyl)piperazin-1-yl)methyl)furan-2-carboxylate (4.558 g, 13.72 mmol), 2-methylpropan-2-amine (1.003 g, 13.72 mmol, 1.441 mL) and triethylamine (4.16 g, 41.1 mmol, 5.72 mL) in dichloromethane was added 1-propanephosphonic acid cyclic anhydride (17.46 g, 27.4 mmol, 16.33 mL, 50% solution in ethyl acetate). The reaction was stirred for 2 hours then concentrated under reduced pressure. The residue was taken up in ethyl acetate, washed with sodium bicarbonate, water and brine. The organic phase was concentrated under reduced pressure to give the title compound (2.4 g). MS (ESI) m/z 366.3 [M+H]+

D: N-tert-Butyl-5-(piperazin-1-ylmethyl)furan-2-carboxamide

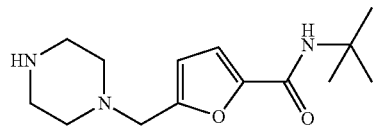 [SMILES: CC(C)(C)NC(=O)c1ccc(CN2CCNCC2)o1]

Tert-butyl 4-((5-(tert-butylcarbamoyl)furan-2-yl)methyl)piperazine-1-carboxylate (6.57 mmol, 2.4 g) was dissolved in dichloromethane (20 mL). 2,2,2-Trifluoro-acetic acid (20 mL) was added and the reaction mixture was stirred for 2 hours. The reaction was concentrated under reduced pressure and purified by SCX chromatography to give the title compound (1.51 g). MS (ESI) m/z 266.4 [M+H]+

E: 5-((4-(4-Amino-3-fluorobenzoyl)piperazin-1-yl)methyl)-N-tert-butylfuran-2-carboxamide

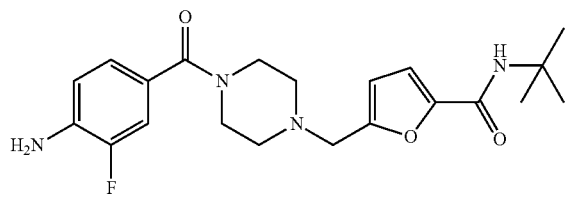 [SMILES: CC(C)(C)NC(=O)c1ccc(CN2CCN(C(=O)c3ccc(N)c(F)c3)CC2)o1]

To a solution of 4-amino-3-fluorobenzoic acid (0.883 g, 5.69 mmol), N-tert-butyl-5-(piperazin-1-ylmethyl)furan-2-carboxamide (1.51 g, 5.69 mmol) and triethyl-amine (0.576 g, 5.69 mmol, 0.791 mL) in dichloromethane was added 1-propanephosphonic acid cyclic anhydride (3.62 g, 5.69 mmol, 3.39 mL, 50% solution in ethyl acetate). The reaction was stirred for 2 hours then concentrated under reduced pressure. The residue was taken up in ethyl acetate, washed with sodium bicarbonate, water and brine. The organic phase was concentrated under reduced pressure to give the title compound (0.93 g). MS (ESI) m/z 403.6 [M+H]+

F: N-tert-Butyl-5-((4-(4-(3-cyclobutylureido)-3-fluorobenzoyl)piperazin-1-yl)methyl)furan-2-carboxamide 5-((4-(4-amino-3-fluorobenzoyl)piperazin-1-yl)methyl)-N-tert-butylfuran-2-carboxamide (113 mg, 0.280 mmol) and 4-nitrophenol chloroformate (56 mg, 0.238 mmol) were combined and stirred in dichloromethane for 1 hour at room temperature. Cyclobutylamine (59.6 mg, 0.839 mmol, 71.6 µl) was added and the reaction was stirred for 30 minutes. The reaction mixture was diluted with water and flushed through a hydrophobic frit. The organic phase was concentrated under vacuum and purified by acidic reverse phase HPLC to afford the title compound (10 mg). MS (ESI) m/z 500.3 [M+H]+

The following compound was prepared in a similar manner:
3B: N-tert-Butyl-5-((4-(3-fluoro-4-(3-isopentylureido)benzoyl)piperazin-1-yl)methyl)furan-2-carboxamide

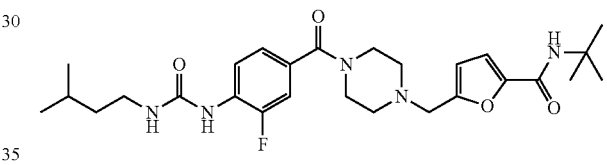

MS (ESI) m/z 516.5 [M+H]+

Example 4

N-tert-Butyl-5-((4-(3-fluoro-4-(3-isobutylureido)benzoyl)piperazin-1-yl)methyl)furan-2-carboxamide

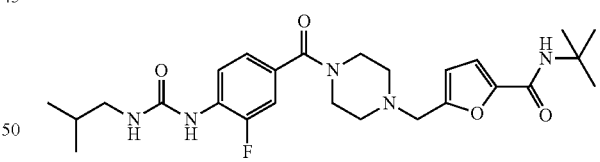

5-((4-(4-Amino-3-fluorobenzoyl)piperazin-1-yl)methyl)-N-tert-butylfuran-2-carboxamide (Example 3; 0.05 g, 0.124 mmol) and N,N-diisopropylethylamine (0.028 mL) were dissolved in dichloromethane (5 mL). Bis(trichloromethyl)carbonate (0.014 g, 0.046 mmol) was added dropwise and the reaction was left to stir for 30 minutes. N,N-diisopropylethylamine (0.094 mL) was added to the reaction followed by 2-methylpropan-1-amine (0.018 g, 0.248 mmol, 0.025 mL) and the reaction was stirred for a further 2 hours. The reaction mixture was washed with water and flushed through a hydrophobic frit. The organic phase was concentrated under vacuum and purified by basic reverse phase HPLC to afford the title compound (5 mg).
MS (ESI) m/z 502.5 [M+H]+

The following compounds were prepared in a similar manner:

4B: N-tert-Butyl-5-((4-(4-(3-(cyclopropylmethyl)ureido)-3-fluorobenzoyl)piperazin-1-yl)methyl)furan-2-carboxamide
MS (ESI) m/z 500.5 [M+H]+

4C: N-tert-Butyl-5-((4-(3-fluoro-4-(3-neopentylureido)benzoyl)piperazin-1-yl)methyl)furan-2-carboxamide
MS (ESI) m/z 516.3 [M+H]+

Example 5

The following compounds were prepared using methods similar to those described in Examples 1-4:

5A: N-tert-Butyl-5-((4-(4-(3-butylureido)-3-fluorobenzoyl)piperazin-1-yl)methyl)furan-2-carboxamide hydrochloride
MS (ESI) m/z 502.5 [M+H]+

5B: N-Cyclobutyl-5-((4-(4-(3-cyclobutylureido)-3-fluorobenzoyl)piperazin-1-yl)methyl)furan-2-carboxamide
MS (ESI) m/z 498.5 [M+H]+

5C: N-Cyclobutyl-5-((4-(3-fluoro-4-(3-isobutylureido)benzoyl)piperazin-1-yl)methyl)furan-2-carboxamide
MS (ESI) m/z 500.4 [M+H]+

5D: (R)—N-sec-Butyl-5-((4-(4-(3-(cyclopropylmethyl)ureido)benzoyl)piperazin-1-yl)methyl)furan-2-carboxamide
MS (ESI) m/z 482.4 [M+H]+

5E: 5-((4-(4-(3-(Cyclopropylmethyl)ureido)-3-fluorobenzoyl)piperazin-1-yl)methyl)-N-(1-methylcyclopropyl)furan-2-carboxamide
MS (ESI) m/z 498.5 [M+H]+

5F: 5-((4-(4-(3-(Cyclopropylmethyl)ureido)-3-fluorobenzoyl)piperazin-1-yl)methy)-N-(3,3-difluorocyclobutyl)furan-2-carboxamide
MS (ESI) m/z 534.3 [M+H]+

5G: N-tert-Butyl-5-((4-(3-chloro-4-(3-neopentylureido)benzoyl)piperazin-1-yl)methyl)furan-2-carboxamide
MS (ESI) m/z 532.5 [M+H]+

5H: N-tert-Butyl-5-((4-(3-chloro-4-(3-isobutylureido)benzoyl)piperazin-1-yl)methyl)furan-2-carboxamide
MS (ESI) m/z 518.8 [M+H]+

5I: N-tert-Butyl-5-((4-(3-chloro-4-(3-(cyclopropylmethyl)ureido)benzoyl)piperazin-1-yl)methyl)furan-2-carboxamide
MS (ESI) m/z 516.5 [M+H]+

5J: N-tert-Butyl-5-((4-(3-chloro-4-(3-isopentylureido)benzoyl)piperazin-1-yl)methyl)furan-2-carboxamide
MS (ESI) m/z 532.3 [M+H]+

5K: N-tert-Butyl-5-((4-(4-(3-butylureido)-3-chlorobenzoyl)piperazin-1-yl)methyl)furan-2-carboxamide
MS (ESI) m/z 518.5 [M+H]+

5L: N-tert-Butyl-5-((4-(3-chloro-4-(3-cyclobutylureido)benzoyl)piperazin-1-yl)methyl)furan-2-carboxamide
MS (ESI) m/z 516.5 [M+H]+

5M: N-tert-Butyl-5-((4-(3-chloro-4-(3-(2-hydroxy-2-methylpropyl)ureido)benzoyl)piperazin-1-yl)methyl)furan-2-carboxamide
MS (ESI) m/z 534.5 [M+H]+

5N: N-tert-Butyl-5-((4-(3-chloro-4-(3-((1-hydroxycyclopropyl)methyl)ureido)benzoyl)piperazin-1-yl)methyl)furan-2-carboxamide

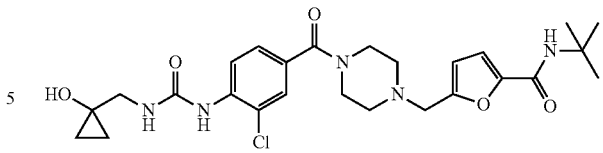

MS (ESI) m/z 532.3 [M+H]+

5O: N-tert-Butyl-5-((4-(3-chloro-4-(3-((1-isocyanocyclopropyl)methyl)ureido)benzoyl)piperazin-1-yl)methyl)furan-2-carboxamide

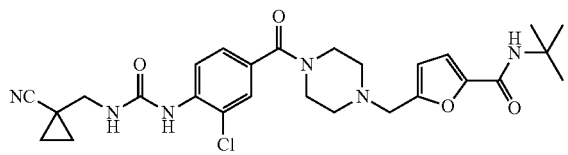 [SMILES: CC(C)(C)NC(=O)c1ccc(CN2CCN(C(=O)c3ccc(NC(=O)NCC4(C#N)CC4)c(Cl)c3)CC2)o1]

MS (ESI) m/z 541.5 [M+H]+

The 1-(aminomethyl)cyclopropanecarbonitrile, needed in the synthesis was prepared as follows:

Step 1: To a mixture of ethyl 1-cyanocyclopropanecarboxylate (35.9 mmol, 5 g), dimethoxyethane (100 mL) and methanol (10 mL) was added sodium borohydride (287 mmol, 10.87 g) slowly and the mixture stirred at room temperature for 18 hours. The solution was diluted with saturated sodium hydrogen carbonate slowly and then extracted with 10% methanol/dichloromethane (×3). The organic layers were combined, dried over sodium sulphate and concentrated under vacuum to give the intermediate 1-(hydroxymethyl)cyclopropanecarbonitrile (2.36 g).

$^1$H NMR (CDCl$_3$, 400 MHz): δ 0.99 (2H, m), 1.28 (2H, m), 2.5 (1H, br s), 3.62 (2H, s)

Step 2: A stirred mixture of 1-(hydroxymethyl)cyclopropanecarbonitrile (24.30 mmol, 2.36 g) in dichloromethane (30 mL) was treated with triethylamine (48.6 mmol, 6.83 mL, 4.92 g) and portionwise with methanesulfonyl chloride (31.6 mmol, 2.445 mL, 3.62 g) keeping the reaction mixture at 0° C. The solution was allowed to stir for 1 hour then diluted with saturated sodium hydrogencarbonate and extracted with 10% methanol/dichloromethane (×3). The organic layers were combined and concentrated under reduced pressure to give the intermediate (1-cyanocyclopropyl)methyl methanesulfonate (3.77 g).

$^1$H NMR (CDCl$_3$, 400 MHz): δ 1.18 (2H, m), 1.46 (2H, m), 3.14 (3H, s), 4.18 (2H, s)

Step 3: A stirred mixture of (1-cyanocyclopropyl)methyl methanesulfonate (21.52 mmol, 3.77 g) and sodium azide (43.0 mmol, 2.80 g) in N,N-dimethyl formamide (40 mL) was heated to 120° C. for ~18 hours. The mixture was allowed to cool and was diluted with water and ethyl acetate. The organic layer was separated, dried over sodium sulphate and concentrated under reduced pressure to give an oil. This oil was taken up in ether and washed with water, dried and concentrated under reduced pressure to give the intermediate 1-(azidomethyl)cyclopropanecarbonitrile (1.8 g) as an oil.

$^1$H NMR (CDCl$_3$, 400 MHz): δ 1.02 (2H, m), 1.36 (2H, m), 3.38 (2H, s)

Step 4: To a solution of 1-(azidomethyl)cyclopropanecarbonitrile (14.74 mmol, 1.8 g) in methanol (20 mL) was added 10% palladium on carbon (14.74 mmol, 200 mg) containing water (200 μL). The mixture was stirred under hydrogen at 3 bar overnight at room temperature. The catalyst was removed by filtration and the filtrate concentrated under reduced pressure to give the title compound (1.3 g).

$^1$H NMR (CDCl$_3$, 400 MHz): δ 0.87 (2H, m), 1.23 (2H, m), 2.76 (2H, s)

5P: N-tert-Butyl-5-((4-(4-(3-(cyclopropylmethyl)ureido)-2,3-difluorobenzoyl)piperazin-1-yl)methyl)furan-2-carboxamide
MS (ESI) m/z 518.5 [M+H]$^+$ 5Q: N-tert-Butyl-5-((4-(2,3-difluoro-4-(3-neopentylureido)benzoyl)piperazin-1-yl)methyl)furan-2-carboxamide
MS (ESI) m/z 534.5 [M+H]$^+$ 5R: N-tert-Butyl-5-((4-(4-(3-butylureido)-2,3-difluorobenzoyl)piperazin-1-yl)methyl)furan-2-carboxamide
MS (ESI) m/z 520.3 [M+H]$^+$ 5S: N-tert-Butyl-5-((4-(2,3-difluoro-4-(3-isobutylureido)benzoyl)piperazin-1-yl)methyl)furan-2-carboxamide
MS (ESI) m/z 520.7 [M+H]$^+$ 5T: N-tert-butyl-5-((4-(2,3-difluoro-4-(3-isopentylureido)benzoyl)piperazin-1-yl)methyl)furan-2-carboxamide
MS (ESI) m/z 534.3 [M+H]$^+$ 5U: N-tert-Butyl-5-((4-(4-(3-cyclobutylureido)-2,3-difluorobenzoyl)piperazin-1-yl)methyl)furan-2-carboxamide
MS (ESI) m/z 518.5 [M+H]$^+$ Example 6

5-((4-(4-(3-(Cyclopropylmethyl)ureido)benzoyl)piperazin-1-yl)methyl)-N-tert-pentylthiophene-2-carboxamide

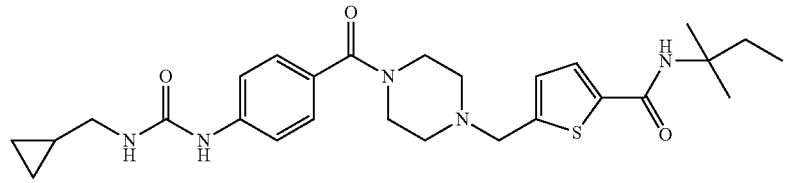 [SMILES: CCC(C)(C)NC(=O)c1ccc(CN2CCN(C(=O)c3ccc(NC(=O)NCC4CC4)cc3)CC2)s1]

A: Ethyl 4-(3-(cyclopropylmethyl)ureido)benzoate

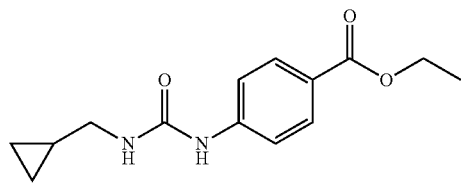 [SMILES: CCOC(=O)c1ccc(NC(=O)NCC2CC2)cc1]

To cyclopropylmethanamine (57.5 mmol, 4.99 ml, 4.09 g) in dichloromethane (40 mL) was added to ethyl 4-isocyanatobenzoate (52.3 mmol, 10 g) in dichloromethane (45 mL) and the reaction stirred overnight. The reaction was then concentrated under reduced pressure to give the title compound (14.7 g).

$^1$H NMR (CDCl$_3$, 400 MHz): δ 0.2 (2H, m) 0.5, (2H, m) 0.95 (1H, m) 1.4 (3H, t), 3.1 (2H, m) 4.35 (2H, q), 5.15 (1H, br s), 7.0, 1H, 7.4 (2H, d) 8.0 (2H, d)

B: 4-(3-(Cyclopropylmethyl)ureido)benzoic acid

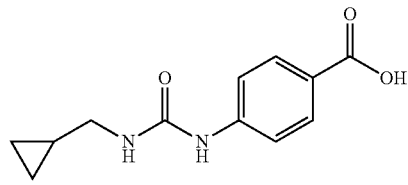 [SMILES: O=C(NCC1CC1)Nc1ccc(C(=O)O)cc1]

Ethyl 4-(3-(cyclopropylmethyl)ureido)benzoate (55.3 mmol, 14.5 g) was suspended in ethanol (400 ml) and 4M sodium hydroxide (332 mmol, 83 mL) added. The reaction was then refluxed until complete saponification was achieved. The ethanol was removed by evaporation and the reaction neutralised with concentrated hydrochloric acid. The white precipitate was collected and washed with water. The material was dried under vacuum to give the title compound (12.19 g)

$^1$H NMR ((CD$_3$)$_2$SO, 400 MHz): δ 0.2 (2H, m) 0.5, (2H, m) 0.95 (1H, m), 3.0 (2H, m) 6.35 (1H, br s) 7.4 (2H, d) 7.8 (2H, d) 8.9 (1H, br s)

C: tert-Butyl 4-(4-(3-(cyclopropylmethyl)ureido)benzoyl)piperazine-1-carboxylate

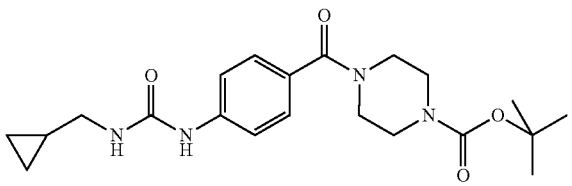 [SMILES: CC(C)(C)OC(=O)N1CCN(C(=O)c2ccc(NC(=O)NCC3CC3)cc2)CC1]

tert-Butyl piperazine-1-carboxylate (45.8 mmol, 8.53 g) and 4-(3-(cyclopropylmethyl)ureido)benzoic acid (45.8 mmol, 10.73 g) were mixed in dichloromethane (200 mL) and triethylamine (103 mmol, 14.36 ml, 10.43 g) added followed by 1-propanephosphonic acid cyclic anhydride (68.7 mmol, 40.7 mL, 43.7 g, 50% solution in ethyl acetate). The reaction was stirred for 1 hour and then was poured into saturated sodium hydrogen carbonate solution and extracted with dichloromethane. The organic phase was dried (magnesium

D: 1-(Cyclopropylmethyl)-3-(4-(piperazine-1-carbonyl)phenyl)urea

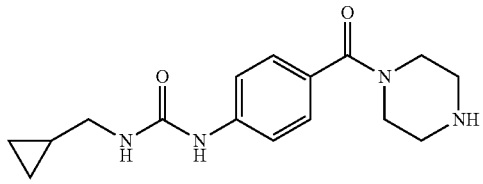 [SMILES: O=C(NCC1CC1)Nc1ccc(C(=O)N2CCNCC2)cc1]

tert-Butyl 4-(4-(3-(cyclopropylmethyl)ureido)benzoyl)piperazine-1-carboxylate (46.7 mmol, 18.78 g) was dissolved in dichloromethane (30 mL) and trifluoroacetic acid (233 mmol, 17.33 ml, 26.6 g) was added. The reaction was stirred for 1 hour and then was concentrated under reduced pressure. The crude material was triturated with ether to give a white powder after high vacuum drying. The white powder was taken up in water and carefully taken to pH 10 with sodium carbonate. The aqueous was then extracted with dichloromethane and the combined organic phases were dried, filtered and concentrated under reduced pressure to give the title compound (13.4 g).

$^1$H NMR (CDCl$_3$, 400 MHz): δ 0.2 (2H, m) 0.5, (2H, m) 0.95 (1H, m) 2.2 (2H, s, br), 2.8 (4H, br s), 3.6 (4H, br s), 5.8 (1H, m) 7.2 (4H, m)

E: Methyl 5-((4-(4-(3-(cyclopropylmethyl)ureido)benzoyl)piperazin-1-yl)methyl)thiophene-2-carboxylate

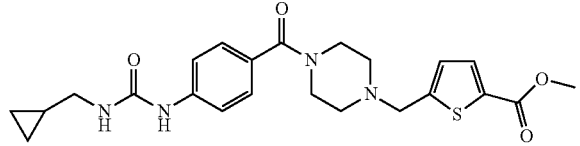 [SMILES: COC(=O)c1ccc(CN2CCN(C(=O)c3ccc(NC(=O)NCC4CC4)cc3)CC2)s1]

1-(Cyclopropylmethyl)-3-(4-(piperazine-1-carbonyl)phenyl)urea (4.25 mmol, 1.286 g), methyl 5-(bromomethyl)thiophene-2-carboxylate (4.25 mmol, 1 g) and potassium carbonate (12.76 mmol, 1.764 g) were stirred at room temperature in acetonitrile (20 mL) for 18 hours. The reaction mixture was concentrated at reduced pressure and the resulting residue taken up in dichloromethane, washed with water, dried over sodium sulfate and concentrated under vacuum to afford the title compound (1.764 g). MS (ESI) m/z 457.5 [M+H]$^+$

F: 5-((4-(4-(3-(Cyclopropylmethyl)ureido)benzoyl)piperazin-1-yl)methyl)thiophene-2-carboxylic acid Methyl 5-((4-(4-(3-(cyclopropylmethyl)ureido)benzoyl)piperazin-1-yl)methyl)-thiophene-2-carboxylate (3.86 mmol, 1.764 g) and sodium hydroxide (3.86 mmol, 0.155 g) were combined and heated to reflux in methanol for 18 hours. The reaction mixture was concentrated at reduced pressure and the resulting residue purified by SCX column chromatography to afford the title compound (1.00 g).
MS (ESI) m/z 443.3 [M+H]$^+$

G: 5-((4-(4-(3-(Cyclopropylmethyl)ureido)benzoyl)piperazin-1-yl)methyl)-N-tert-pentylthiophene-2-carboxamide 5-((4-(4-(3-(Cyclopropylmethyl)ureido)benzoyl)piperazin-1-yl)methyl)-thiophene-2-carboxylic acid (100 mg, 0.226 mmol), N,N-diisopropylethylamine (99 mg, 0.127 mL, 0.452 mmol) and tert-pentylamine (39 mg, 0.452 mmol) were combined and stirred in dichloromethane. 1-Propanephosphonic acid cyclic anhydride (216 mg, 0.202 mL, 0.339 mmol, 50% solution in ethyl acetate) was added and the reaction stirred for 1 hour at room temperature. The reaction mixture was washed with saturated sodium bicarbonate solution, dried over sodium sulfate, concentrated under vacuum and purified by reverse phase acidic preparative HPLC to afford the title compound (5 mg). MS (ESI) m/z 512.8 [M+H]$^+$ The following compound was prepared in a similar manner:

6B: N-tert-butyl-5-((4-(4-(3-(cyclopropylmethyl)ureido)benzoyl)piperazin-1-yl)methyl)thiophene-2-carboxamide
MS (ESI) m/z 498.5 [M+H]$^+$

Example 7

N-tert-Butyl-3-((4-(4-(3-cyclobutylureido)-3-fluorobenzoyl)piperazin-1-yl)methyl)-1H-pyrazole-1-carboxamide

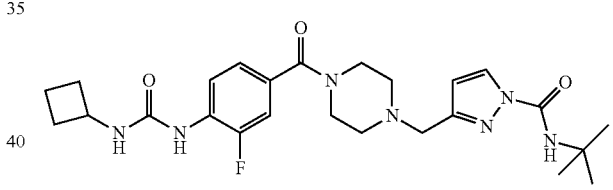

A:
N-tert-Butyl-3-methyl-1H-pyrazole-1-carboxamide

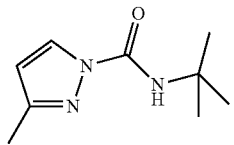

To tert-butyl isocyanate (1.57 mL, 1.34 g, 13.70 mmol) in dichloromethane (30 mL) was added 3-methyl-1H-pyrazole (0.98 mL, 1 g, 12.18 mmol). The mixture was stirred overnight at room temperature and then concentrated under vacuum. The crude material was purified by silica chromatography (eluting with dichloromethane) to give the title compound (2.1 g).

$^1$H NMR (CD$_3$OD, 400 MHz): δ 1.46 (9H, s), 2.28 (3H, s), 6.14 (2H, d), 7.02 (1H, br s), 8.08 (1H, d)

B: 3-(Bromomethyl)-N-tert-butyl-1H-pyrazole-1-carboxamide

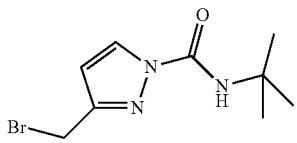

To N-tert-butyl-3-methyl-1H-pyrazole-1-carboxamide (609 mg, 3.36 mmol) in carbon tetrachloride (12 mL) was added N-bromosuccinimide (849 mg, 4.77 mmol) and benzoyl peroxide (114 mg, 0.470 mmol). The mixture was heated to reflux overnight and then diluted with water and ethyl acetate. The organic layer was separated, dried and concentrated under reduced pressure. The crude material was purified by silica chromatography (eluting with 10% ethyl acetate in heptane) to give the title compound (280 mg).

$^1$H NMR (CDCl$_3$, 400 MHz): δ 1.47 (9H, s), 4.43 (2H, d), 6.42 (1H, d), 6.99 (1H, br s), 8.14 (1H, d)

C: tert-Butyl 4-(4-amino-3-fluorobenzoyl)piperazine-1-carboxylate

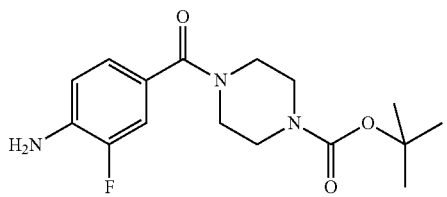 [SMILES: CC(C)(C)OC(=O)N1CCN(C(=O)c2ccc(N)c(F)c2)CC1]

To a stirred solution of 4-amino-3-fluorobenzoic acid (4.97 g, 32.04 mmol), tert-butyl piperazine-1-carboxylate (5.97 g, 32.04 mmol) and triethylamine (10 mL) in dichloromethane (100 mL) was added 1-propanephosphonic acid cyclic anhydride (20 mL, 50% solution in ethyl acetate, dropwise). The reaction mixture was stirred for 1 hour then was diluted with ethyl acetate, washed with potassium carbonate (aqueous), dried (magnesium sulfate) and concentrated under reduced pressure to give the title compound (9.5 g). MS (ESI) m/z: 324.5 [M+H]$^+$.

D: tert-Butyl 4-(4-(3-cyclobutylureido)-3-fluorobenzoyl)piperazine-1-carboxylate

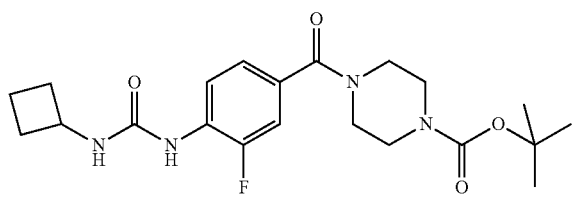 [SMILES: CC(C)(C)OC(=O)N1CCN(C(=O)c2ccc(NC(=O)NC3CCC3)c(F)c2)CC1]

tert-Buty 4-(4-amino-3-fluorobenzoyl)piperazine-1-carboxylate (9.5 g, 29.41 mmol) was dissolved in dichloromethane (100 mL) and 4-nitrophenyl carbonochloridate (5.93 g, 29.41 mmol) was added. The reaction mixture was stirred for 20 hours and cyclobutylamine (7.5 mL, 88.2 mmol) added. After 2 hours, the reaction mixture was chromatographed on silica (eluting with dichloromethane to dichloro-methane/ethyl acetate) to give the title compound (2.8 g). MS (ESI) m/z: 421.0 [M+H]$^+$

E: 1-Cyclobutyl-3-(2-fluoro-4-(piperazine-1-carbonyl)phenyl)urea tert-Butyl 4-(4-(3-cyclobutylureido)-3-fluorobenzoyl)piperazine-1-carboxylate (2.8 g, 66.67 mmol), trifluoracetic acid and dichloromethane were stirred for 20 hours then concentrated under reduced pressure. The residue was taken up in dichloromethane/methanol, loaded on to a strong cation exchange column and washed with dichloromethane/methanol. Elution of the column with 2M ammonia in methanol gave the title compound (1.6 g). MS (ESI) m/z: 321.4 [M+H]$^+$

F: N-tert-Butyl-3-((4-(4 (3-cyclobutylureido)-3-fluorobenzo)piperazin-1-yl)methyl)-1H-pyrazole-1-carboxamide To 3-(bromomethyl)-N-tert-butyl-1H-pyrazole-1-carboxamide (102 mg, 0.392 mmol) in acetonitrile (3.9 mL) was added 1-cyclobutyl-3-(2-fluoro-4-(piperazine-1-carbonyl)phenyl)urea (126 mg, 0.392 mmol), and triethylamine (109 μl, 79 mg, 0.782 mmol). To this mixture was added a spatula tip of sodium iodide. The mixture was heated to reflux overnight and was then diluted with water and ethyl acetate. The organic layer was separated, dried and concentrated under reduced pressure. The residue was purified by silica chromatography, eluting with 2% methanol in dichloromethane. The residue was taken up in dichloromethane/methanol, loaded on to a strong cation exchange column and washed with dichloromethane/methanol. Elution of the column with 2M ammonia in methanol gave the title compound (44 mg).

MS (ESI) m/z 500.3 [M+H]$^+$

Example 8

N-tert-Butyl-4-((4-(4-(3-cyclobutylureido)-3-fluorobenzoyl)piperazin-1-yl)methyl)picolinamide

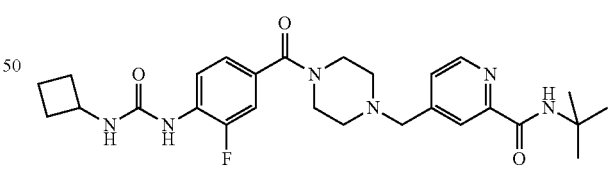

A: N-tert-Butyl-4-methylpicolinamide

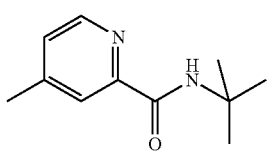

4-Methylpyridine-2-carboxylic acid (500 mg, 3.65 mmol), triethylamine (1.27 g, 12.5 mmol, 1.75 mL) and tert-butylamine (267 mg, 3.65 mmol) were combined and stirred in dichloromethane (1 mL). 1-Propanephosphonic acid cyclic anhydride (4.82 g, 7.5 mmol, 4.5 mL, 50% solution in ethyl acetate) was added dropwise and the reaction stirred at room temperature for 1 hour. The reaction mixture was concentrated at reduced pressure and the resulting residue taken up in ethyl acetate and washed with saturated sodium bicarbonate solution. The organic phase was dried over sodium sulfate and concentrated under vacuum to afford the title compound (376 mg). MS (ESI) m/z 193.4 [M+H]$^+$ B: 4-Bromomethyl)-N-tert-butylpicolinamide

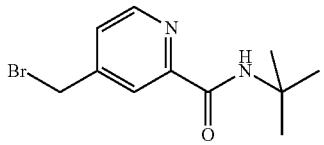

N-tert-Butyl-4-methylpicolinamide (100 mg, 0.52 mmol) and N-bromosuccinimide (46 mg, 0.52 mmol) were combined in chlorobenzene (5 mL) and stirred under a sunlamp for 1 hour. The reaction mixture was concentrated at reduced pressure. The resulting residue was taken up in dichloromethane and washed with water. The organic phase was dried over sodium sulfate and concentrate under vacuum to afford the title compound (120 mg). MS (ESI) m/z 271.5 [M+H]$^+$ C: N-tert-butyl-4-((4-(4-(3-cyclobutylureido)-3-fluorobenzoyl)piperazin-1-yl)methyl)picolinamide 4-(Bromomethyl)-N-tert-butylpicolinamide (70 mg, 0258 mmol), 1-(cyclobutyl-methyl)-3-(2-fluoro-4-(piperazine-1-carbonyl)phenyl)urea (83 mg, 0.258 mmol) and potassium carbonate (106 mg, 0.744 mmol) were combined and heated to reflux in acetonitrile for 1 hour. The reaction mixture was concentrated at reduced pressure and the resulting residue purified by reverse phase acidic preparative HPLC to afford the title compound (41 mg). MS (ESI) m/z 511.6 [M+H]$^+$ Example 9

N-tert-Butyl-6-((4-(4-(3-cyclobutylureido)-3-fluorobenzoyl)piperazin-1-yl)methyl)picolinamide

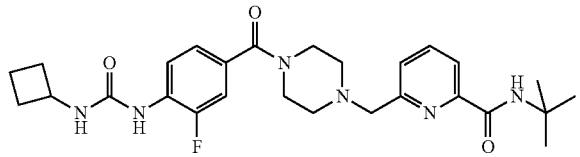 [SMILES: CC(C)(C)NC(=O)c1cccc(CN2CCN(C(=O)c3ccc(NC(=O)NC4CCC4)c(F)c3)CC2)n1]

A: Methyl 6-((methylsulfonyloxy)methyl)picolinate

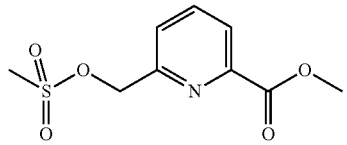

6-(Hydroxymethyl)picolinate (200 mg, 1.196 mmol) and triethylamine (363 mg, 3.588 mmol, 0.5 mL) were combined and stirred at 0° C. in dichloromethane (2 mL). Methanesulfonyl chloride (206 mg, 1.794 mmol) was added and the reaction allowed to warm to room temperature over 1 hour. The reaction was washed with water, dried over sodium sulfate and concentrated under vacuum to afford the title compound (293 mg). MS (ESI) m/z 246.3 [M+H]$^+$ B: Methyl 6-((4-(4-(3-cyclobutylureido)-3-fluorobenzoyl)piperazin-1-yl)methyl)picolinate

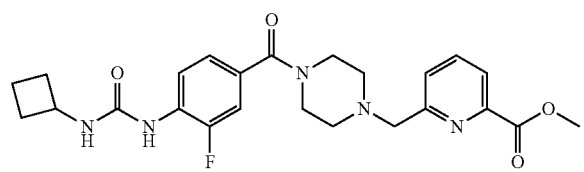 [SMILES: COC(=O)c1cccc(CN2CCN(C(=O)c3ccc(NC(=O)NC4CCC4)c(F)c3)CC2)n1]

Methyl 6-((methylsulfonyloxy)methyl)picolinate (300 mg, 1.22 mmol), 1-(cyclo-butylmethyl)-3-(2-fluoro-4-(piperazine-1-carbonyl)phenyl)urea (391 mg, 1.22 mmol) and potassium carbonate (505 mg, 3.66 mmol) were combined and stirred in acetonitrile for 18 hours. The reaction mixture was concentrated at reduced pressure. The resulting residue was taken up in dichloromethane, washed with water, dried over sodium sulfate and concentrated under vacuum to afford the title compound (407 mg).
MS (ESI) m/z 470.5 [M+H]$^+$ C: Sodium 6-((4-(4-(3-cyclobutylureido)-3-fluorobenzoyl)piperazin-1-yl)methyl)picolinate Methyl 6-((4-(4-(3-cyclobutylureido)-3-fluorobenzoyl)piperazin-1-yl)methyl)picolinate (400 mg, 0.852 mmol) and sodium hydroxide (35 mg, 0.852 mmol) were combined and heated to reflux for 18 hours in methanol. The reaction mixture was concentrated at reduced pressure to afford the title compound (323 mg).
MS (ESI) m/z 456.5 [M+H]$^+$ D: N-tert-Butyl-6-((4-(4-(3-cyclobutylureido)-3-fluorobenzoyl)piperazin-1-yl)methyl)picolinamide Sodium 6-((4-(4-(3-cyclobutylureido)-3-fluorobenzoyl)piperazin-1-yl)methyl)-picolinate (100 mg, 0.209 mmol), triethylamine (66 mg, 0.693 mmol, 0.091 mL) and tert-butylamine (32 mg, 0.435 mmol) were combined and stirred at room temperature in dichloromethane. 1-Propanephosphonic acid cyclic anhydride (208 mg, 0.326 mmol, 0.194 mL, 50% solution in ethyl acetate) was added dropwise and the reaction allowed to stir for 1 hour. The reaction mixture was concentrated at reduced pressure, the resulting residue taken up in ethyl acetate and washed with saturated sodium bicarbonate solution. The organic phase was dried over sodium sulfate and concentrated under vacuum to afford the title compound (24 mg). MS (ESI) m/z 511.6 [M+H]+

The following compounds were prepared using similar methods:

9B: N-tert-Butyl-6-((4-(3-fluoro-4-(3-neopentylureido)benzoyl)piperazin-1-yl)methyl)picolinamide
MS (ESI) m/z 527.0 [M+H]+

9C: N-tert-Butyl-6-((4-(3-fluoro-4-(3-isopentylureido)benzoyl)piperazin-1-yl)methyl)picolinamide
MS (ESI) m/z 527.0 [M+H]+

9D: N-tert-Butyl-6-((4-(4-(3-(cyclopropylmethyl)ureido)-3-fluorobenzoyl)piperazin-1-yl)methyl)picolinamide
MS (ESI) m/z 511.3 [M+H]+

Example 10

N-tert-butyl-2-((4-(4-(3-cyclobutylureido)-3-fluorobenzoyl)piperazin-1-yl)methyl)isonicotinamide

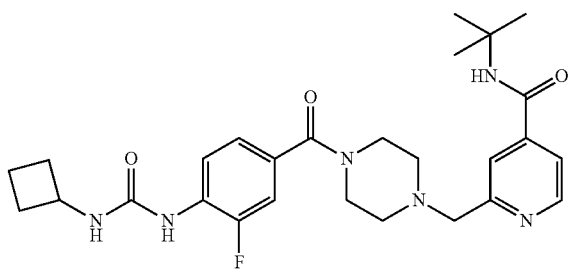 [SMILES: CC(C)(C)NC(=O)c1ccnc(CN2CCN(C(=O)c3ccc(NC(=O)NC4CCC4)c(F)c3)CC2)c1]

A: Methyl 2-((methylsulfonyloxy)methyl)isonicotinate

Methyl 2-(hydroxymethyl)isonicotinate (3.17 mmol, 0.530 g) and triethylamine (9.51 mmol, 1.322 mL, 0.963 g) were stirred in dichloromethane (20 mL) at 0° C. Methanesulfonyl chloride (4.76 mmol, 0.368 mL, 0.545 g) was added dropwise and the reaction stirred at room temperature for 1 hour. The reaction mixture was washed with water, dried over sodium sulfate and concentrated under vacuum to afford the title compound (686 mg). MS (ESI) m/z 246.4 [M+H]+

B: Methyl 2-((4-(4-(3-cyclobutylureido)-3-fluorobenzoyl)piperazin-1-yl)methyl)isonicotinate Methyl 2-(methylsulfonylmethyl)isonicotinate (2.99 mmol, 0.686 g), 1-cyclobutyl-3-(2-fluoro-4-(piperazine-1-carbonyl)phenyl)urea (2.99 mmol, 0.959 g) and potassium carbonate (8.98 mmol, 1.241 g) were combined and heated to 40° C. in acetonitrile (20 mL) for 2 hours. The reaction mixture was concentrated at reduced pressure and the residue taken up in dichloromethane. The organic phase was dried over sodium sulfate and concentrated under vacuum. The residue was purified by silica chromatography (eluting with a solvent gradient from dichloromethane to 6% methanol/dichloromethane) to afford the title compound (822 mg). MS (ESI) m/z 470.5 [M+H]+

C: Sodium 2-((4-(4-(3-cyclobutylureido)-3-fluorobenzoyl)piperazin-1-yl)methyl)isonicotinate Methyl 2-((4-(4-(3-cyclobutylureido)-3-fluorobenzoyl)piperazin-1-yl)methyl)isonicotinate (1.746 mmol, 0.82 g) and sodium hydroxide (1.746 mmol, 0.070 g) were heated to reflux in methanol (20 mL) for 18 hours. The reaction mixture was concentrated at reduced pressure to afford the title compound (798 mg).
MS (ESI) m/z 456.5 [M+H]+

D: N-tert-Butyl-2-((4-(3-cyclobutylureido-3-fluorobenzoyl)piperazin-1-yl)methyl)isonicotinamide Sodium 2-((4-(4-(3-cyclobutylureido)-3-fluorobenzoyl)piperazin-1-yl)methyl)isonicotinate (0.209 mmol, 0.1 g), tert-butylamine (0.419 mmol, 0.088 mL, 0.061 g) and triethylamine (0.628 mmol, 0.087 mL, 0.064 g) were stirred in dichloro-methane (10 mL). 1-Propanephosphonic acid cyclic anhydride (0.209 mmol, 0.062 mL, 0.067 g, 50% solution in ethyl acetate) was added and the reaction stirred at room temperature for 1 hour. The reaction mixture was concentrated at reduced pressure. The residue was taken up in ethyl acetate and washed with saturated sodium bicarbonate solution. The organic phase was dried over sodium sulfate and concentrated under vacuum. The resulting residue was purified by reverse phase acidic preparative HPLC to afford the title compound (35 mg). MS (ESI) m/z 511.6 [M+H]+

Example 11

Radioligand Competition Binding Scintillation Proximity Assay (SpA) using Recombinant Human LXRα or LXRβ Protein These assays are used to evaluate the potency of compounds in their ability to compete with the binding of the agonist radioligand [H]T0901317. These assays utilise purified ligand binding domain (LBD) of Liver X Receptor alpha (LXRα)α or Liver X Receptor beta (LXRβ) fused to glutathione-S-transferase (GST) tagged protein (LXRα-LBD-GST and LXRβ-LBD-GST) and scintillation proximity assay (SpA) technology to determine binding affinities (pKi) of compounds at the ligand binding domain (LBD) of the human nuclear hormone receptor LXRα or LXRβ.

Preparation of Recombinant Human LXRα and LXRβ

Human LXRα and LXRβ were expressed as GST-fusion proteins in E. coli. The LBD of LXRα or LXRβ was amplified by PCR and sub-cloned into the prokaryotic expression vector pGEX-4T-1 (GE Healthcare). Expression of LXRα or LXRβ 3 from the pGEX-4T-1 plasmid in E. Coli resulted in the production of the recombinant glutathione-S-transferase (GST) LXRα-LBD or LXRβ-LBD fusion proteins.

E. coli, containing either the LXRα or LXRβ pGEX-4T-1 plasmid, were propagated, induced, and harvested by centrifugation. The bacterial pellets were resuspended in lysis buffer containing 50 mM tris(hydroxymethyl)aminomethane (TRIS)-pH 8.0, 100 mM Sodium Chloride (NaCl), 1 mM ethylenediaminetetraacetic acid (EDTA) and one tablet of proteinase inhibitor cocktail complete/EDTA free (Roche) (per 50 ml of buffer). The mixtures were sonicated on ice with a Branson sonifier. The suspensions were centrifuged and dithiothreitol (DTT) added to the supernatants to obtain a final concentration of 25 mM. Recombinant human LXRα-LBD-GST or LXRβ-LBD-GST proteins were purified from the resulting supernatants by affinity chromatography on glutathione-Sepharose Fast flow (Amersham), and the proteins eluted with buffer containing glutathione (50 mM tris pH 8.0, 2 mM DTT, 10 mM glutathione). Proteins were stored in 20 mM N-2-hydroxyethylpiperazine-N'-2-ethanesulfonic Acid (HEPES), 2 mM DTT with 10% glycerol at −80° C.

Binding to LXRα or LXRβ LBDs

For LXRα or LXRβ assays, an aliquot of recombinant human LXRα-LBD-GST or LXRβ-LBD-GST protein was diluted to 0.5 μg/mL and incubated in a final volume of 100 μl SpA buffer (10 mM potassium hydrogen phosphate anhydrous [$K_2HPO_4$], 10 mM potassium phosphate monobasic [$KH_2PO_4$], 2 mM EDTA pH 7.1, 50 mM NaCL, 1 mM DTT, 2 mM 3-[(3-cholamidopropyl)dimethylammonio]-1-propanesulfonate (CHAPS)) containing Protein-A coupled scintillant filled YtSi SpA beads (GE Healthcare), to a final concentration of 1 mg/ml and goat anti-GST antibody (GE Healthcare) to a final concentration of 5 μg/ml. T0901317 ($K_d$=10 nM) was used as a reference in each assay. To the assay mixture, 50 nM [$^3$H]T0901317 (50 Ci/mmol), ±test compound was added and the mixture incubated at 15° C. on a plate shaker for 2 h. After incubation, the assay plates were read on a Packard TopCount. The pKi value for T0901317 in LXRα and LXRβ binding assays is: pKi=8.4±0.2. T0901317 at a concentration of 5 μM was used as the maximum binding control. Active compounds show pKi values >5.5 at LXRα and/or LXRβ and preferred compounds show pKi values of >7 at LXRα and/or LXRβ in these assays.

LXRα and LXRβ Transactivation Assays

Intracellular agonist activity at LXRα and LXRβ was measured in vitro using recombinant chinese hamster ovary K1 (CHO.K1) cells stably expressing a natural estrogen responsive element (ERE)-containing luciferase reporter construct and either the human Estrogen receptor α (ERα)/LXRα or ERα/LXRβ chimeric receptor protein respectively from a eukaryotic expression construct. The ERα/LXRα and ERα/LXRβ chimeric receptor proteins contain the human LXRα or human LXRβ receptor LBD fused to the human ERα receptor DNA binding domain (DBD). In these assays compounds that can bind to the LBD of the human LXRα or LXRβ receptor, are able to activate the chimeric receptor protein intracellularly. Following activation, the ERα DBD can induce ERE-mediated luciferase expression via the natural ERE present in the rat oxytocin promoter luciferase construct (pROLUC). Using this system LXRα and LXRβ agonist-induced luciferase assays were generated using T0901317 as the agonist control.

Constructs

Expression constructs were prepared by inserting the ligand binding domain (LBD) of human LXRα or human LXRβ cDNA adjacent to the human ERα transcription factor DNA binding domain (DBD) to create pNGV1.ERαDBD-LXRαLBD and pNGV1.ERαDBD-LXRβLBD. The pNGV1 mammalian expression construct (EMBL nucleotide sequence database file ASPNGV1, acc. #X99274) carries a selection marker for Neomycin (G418). The ERα responsive element of the rat oxytocin promoter (RO) was used to generate the promoter construct, pROLUC which contains several copies of the ERα response element (ERE) placed adjacent to the luciferase reporter gene. Construction of the promoter construct was based on the RO promoter region (position −363/+16) excised as a HindIII/MboI restriction enzyme fragment and linked to the firefly luciferase encoding sequence (See Ivell and Richter, *Proc Nat Acad Sci USA*. 7: 2006-2010 (1984)). Stable CHO.K1 cell lines expressing pNGV1.ERαDBD-LXRαLBD or pNGV1.ERαDBD-LXRβLBD in combination with pROLUC were generated following transfection and selection of positive expressing clones using Neomycin. The best cell lines (CHO.K1 LXRα and CHO.K1 LXRβ) were selected on the basis of agonist window in response to 3 μM T0901317 and stability of response up to 20 passages.

Agonist Activity of Test Compounds in LXRα and LXRβ Transactivation Assays

For LXRα and LXRβ transactivation assays CHO.K1 LXRα or CHO.K1 LXRβ cells respectively were seeded at a density of 25000 cells/well in 96 well plates in 200 μl of Dulbecco's Modified Eagle Medium (phenol red free) containing 5% charcoal treated bovine calf serum at 37° C. in a humidified atmosphere of 5% $CO_2$. After 6 h post-seeding, compounds were characterised by incubation with cells for 16 h across a concentration range. T0901317 at a concentration of 3 μM was used as the maximum agonist control in each assay. Luciferase activity was determined using a Luciferase assay kit (Perkin Elmer). Determination of luciferase activity was initiated by addition of lysis buffer to each well and light emission measured using a Packard Topcount reader. The $pEC_{50}$ values for T0901317 in the LXRα and LXRβ 3 transactivation assays are: $pEC_{50}$=7.3±0.2 and 7.4±0.2 respectively. Agonist activities of test compounds were compared against the maximum agonist control. Preferred compounds of the invention were shown to have LXRα and/or LXRβ agonist activity using these assay protocols.

The invention claimed is:

1. A 1-(4-ureidobenzoyl)piperazine derivative having the general formula I

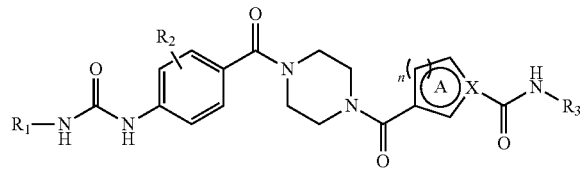

Formula I wherein
R$_1$ is (C$_{1-8}$)alkyl, (C$_{3-8}$)cycloalkyl or (C$_{3-8}$)cycloalkyl(C$_{1-3}$)alkyl, each of which may be substituted by hydroxy, cyano or halogen;
R$_2$ represents 1 or 2 optional halogens;
R$_3$ is (C$_{1-6}$)alkyl, (C$_{3-6}$)cycloalkyl or (C$_{3-6}$)cycloalkyl(C$_{1-3}$)alkyl, each of which may be substituted by one or more halogens;
A represents a heteroaryl ring system comprising 1-3 heteroatoms selected from N, O and S, which ring system is 5- or 6-membered when X is C, and 5-membered when X is N; n is 1 or 2; or a pharmaceutically acceptable salt thereof.

2. The 1-(4-ureidobenzoyl)piperazine derivative of claim 1, wherein A represents furan-2,5-diyl or pyridine-2,6-diyl.

3. The 1-(4-ureidobenzoyl)piperazine derivative of claim 1, wherein R$_2$ represents 1 or 2 halogens selected from F and Cl.

4. The 1-(4-ureidobenzoyl)piperazine derivative of claim 1, wherein R$_3$ is tert-butyl.

5. The 1-(4-ureidobenzoyl)piperazine derivative of claim 1, which is selected from:

N-tert-butyl-5-((4-(4-(3-cyclobutylureido)-3-fluorobenzoyl)piperazin-1-yl)methyl)furan-2-carboxamide;
N-tert-butyl-5-((4-(3-fluoro-4-(3-isobutylureido)benzoyl)piperazin-1-yl)methyl)furan-2-carboxamide;
N-tert-butyl-5-((4-(4-(3-(cyclopropylmethyl)ureido)-3-fluorobenzoyl)piperazin-1-yl)methyl)furan-2-carboxamide;
N-tert-butyl-5-((4-(3-fluoro-4-(3-neopentylureido)benzoyl)piperazin-1-yl)methyl)furan-2-carboxamide;
N-tert-butyl-5-((4-(3-fluoro-4-(3-isopentylureido)benzoyl)piperazin-1-yl)methyl)furan-2-carboxamide;
N-tert-butyl-5-((4-(4-(3-butylureido)-3-fluorobenzoyl)piperazin-1-yl)methyl)furan-2-carboxamide hydrochloride;
N-tert-butyl-5-((4-(3-chloro-4-(3-neopentylureido)benzoyl)piperazin-1-yl)methyl)furan-2-carboxamide;
N-tert-butyl-5-((4-(3-chloro-4-(3-isobutylureido)benzoyl)piperazin-1-yl)methyl)furan-2-carboxamide;
N-tert-butyl-5-((4-(3-chloro-4-(3-(cyclopropylmethyl)ureido)benzoyl)piperazin-1-yl)methyl)furan-2-carboxamide;
N-tert-butyl-5-((4-(3-chloro-4-(3-cyclobutylureido)benzoyl)piperazin-1-yl)methyl)furan-2-carboxamide;
N-tert-butyl-5-((4-(3-chloro-4-(3-isopentylureido)benzoyl)piperazin-1-yl)methyl)furan-2-carboxamide;
N-tert-butyl-5-((4-(4-(3-butylureido)-3-chlorobenzoyl)piperazin-1-yl)methyl)furan-2-carboxamide;
N-tert-butyl-5-((4-(4-(3-(cyclopropylmethyl)ureido)-2,3-difluorobenzoyl)piperazin-1-yl)methyl)furan-2-carboxamide;
N-tert-butyl-5-((4-(2,3-difluoro-4-(3-neopentylureido)benzoyl)piperazin-1-yl)methyl)furan-2-carboxamide;
N-tert-butyl-5-((4-(2,3-difluoro-4-(3-isobutylureido)benzoyl)piperazin-1-yl)methyl)furan-2-carboxamide;
N-tert-butyl-5-((4-(4-(3-cyclobutylureido)-2,3-difluorobenzoyl)piperazin-1-yl)methyl)furan-2-carboxamide;
N-tert-butyl-5-((4-(4-(3-butylureido)-2,3-difluorobenzoyl)piperazin-1-yl)methyl)furan-2-carboxamide;
N-tert-butyl-5-((4-(2,3-difluoro-4-(3-isopentylureido)benzoyl)piperazin-1-yl)methyl)furan-2-carboxamide;
N-tert-butyl-6-((4-(4-(3-cyclobutylureido)-3-fluorobenzoyl)piperazin-1-yl)methyl)picolinamide;
N-tert-butyl-6-((4-(3-fluoro-4-(3-neopentylureido)benzoyl)piperazin-1-yl)methyl)picolinamide;
N-tert-butyl-6-((4-(3-fluoro-4-(3-isopentylureido)benzoyl)piperazin-1-yl)methyl)picolinamide; and
N-tert-butyl-6-((4-(4-(3-(cyclopropylmethyl)ureido)-3-fluorobenzoyl)piperazin-1-yl)methyl)picolinamide; or a pharmaceutically acceptable salt thereof.

6. A pharmaceutical composition comprising a 1-(4-ureidobenzoyl)piperazine derivative of claim 1 or a pharmaceutically acceptable salt thereof and pharmaceutically acceptable auxiliaries.

7. A pharmaceutical composition comprising a 1-(4-ureidobenzoyl)piperazine derivative of claim 5 or a pharmaceutically acceptable salt thereof and pharmaceutically acceptable auxiliaries.

8. A method of treating atherosclerosis in a human patient in need of treatment comprising the administration of a therapeutically effective amount of a 1-(4-ureidobenzoyl)piperazine derivative of claim 1 or a pharmaceutically acceptable salt thereof.

9. A method of treating atherosclerosis in a human patient in need of treatment comprising the administration of a therapeutically effective amount of a 1-(4-ureidobenzoyl)piperazine derivative of claim 5 or a pharmaceutically acceptable salt thereof.

* * * * *